(12) United States Patent
Konkel et al.

(10) Patent No.: US 6,706,716 B2
(45) Date of Patent: Mar. 16, 2004

(54) COMPOUNDS SPECIFIC FOR THE HUMAN $\alpha_{1D}$ ADRENERGIC RECEPTOR AND USES THEREOF

(75) Inventors: Michael Konkel, Garfield, NJ (US); John M. Wetzel, Fair Lawn, NJ (US); Stewart A. Noble, Wheeling, IL (US); Charles Gluchowski, Danville, CA (US); Douglas A. Craig, Emerson, NJ (US)

(73) Assignee: Synaptic Pharmaceutical Corporation, Paramus, NJ (US)

( * ) Notice: Subject to any disclaimer, the term of this patent is extended or adjusted under 35 U.S.C. 154(b) by 0 days.

(21) Appl. No.: 09/764,710

(22) Filed: Jan. 17, 2001

(65) Prior Publication Data

US 2002/0028760 A1 Mar. 7, 2002

Related U.S. Application Data

(63) Continuation of application No. PCT/US99/16101, filed on Jul. 16, 1999, which is a continuation-in-part of application No. 09/118,323, filed on Jul. 17, 1998, now abandoned.

(51) Int. Cl.[7] .................. A61P 43/00; A61K 31/495; C07D 401/02
(52) U.S. Cl. .................. 514/253.11; 514/253.12; 544/360; 544/365
(58) Field of Search .................. 544/365, 360; 514/253.11, 253.12

(56) References Cited

U.S. PATENT DOCUMENTS

| | | |
|---|---|---|
| 3,398,151 A | 8/1968 | Wu |
| 3,558,777 A | 1/1971 | Wu |
| 4,988,700 A | 1/1991 | Traber et al. |
| 5,070,102 A | 12/1991 | Traber et al. |
| 5,096,908 A | 3/1992 | Gidda et al. |
| 5,155,128 A | 10/1992 | Traber et al. |
| 5,200,410 A | 4/1993 | Traber et al. |
| 5,258,379 A | 11/1993 | Gidda et al. |
| 5,294,619 A | 3/1994 | Nagel |

FOREIGN PATENT DOCUMENTS

| | | |
|---|---|---|
| DE | 4039631 | 6/1992 |
| EP | 0372776 | 6/1990 |
| EP | 0395312 | 10/1990 |
| EP | 0447345 | 9/1991 |
| WO | 9957131 | 11/1999 |
| WO | 0105765 | 1/2001 |

OTHER PUBLICATIONS

Wu, et al, J. Med. Chem, 1969, 12, 876–881.*
Goetz, A. S. et al., BMY 7378 is a selective antagonist of the D subtype of $\alpha_1$–adrenoceptors. Eur. J. Pharmacol. (1995) 272: R5–R6.
Lopez–Rodriguez et al., 1–[ω (4–Arylpiperazin- 1–yl)alkyl]– 3–diphenylmethylene–2,5–pyrrolidinediones as 5–HT$_{1A}$ receptor ligands: study of the steric requirements of the terminal amide fragment on 5–HT$_{1A}$ affinity/selectivity. Bioorganic & Medicinal Chemistry Letters (1998) 8: 581–586.
Saussy, D.L. Jr. et al., Structure activity relationships of a series of buspirone analogs at alpha–1 adrenoceptors: Further evidence that rat aorta alpha–1 adrenoceptors are of the alpha–1D–subtype. J. Pharmacol. Exp. Ther. (1996) 278: 136–144.
Snowball, R.K. et al. Investigation of the role of $\alpha_{1A}$– and $\alpha_{1D}$– adrenoceptors in the control of the "micturition reflex" in the anaesthetized male rat. British Journal of Pharmacology, Proceedings of the British Pharmacology Society Meeting Jan. 5–7, 2000, Abstract 35P.
Wu, Y. –H. et al., Psychosedative agents. N–(4–Phenyl–1–piperazinylalkyl)–substituted cyclic imides. J. Med. Chem. (1969) 12: 876–881.

* cited by examiner

*Primary Examiner*—Deborah C. Lambkin
*Assistant Examiner*—Andrea D. Small
(74) *Attorney, Agent, or Firm*—John P. White; Cooper & Dunham LLP

(57) ABSTRACT

This invention is directed towards a method of inhibiting activation of a human $\alpha_{1d}$ adrenergic receptor which comprises contacting the receptor with a compound so as to inhibit activation of the receptor, wherein the compound binds selectively to a human $\alpha_{1d}$ adrenergic receptor. This invention provides for a compound which binds selectively to a human $\alpha_{1d}$ adrenergic receptor. The invention further provides a pharmaceutical composition comprising a therapeutically effective amount of the above-defined compounds and a pharmaceutically acceptable carrier. This invention further provides for a method of treating a subject afflicted with a disease which is susceptible to treatment by antagonism of the human $\alpha_{1d}$ adrenergic receptor which comprises administering to the subject an amount of the above defined compounds effective to treat the disease.

38 Claims, 8 Drawing Sheets

Compound 1

Compound 2

Compound 3

Compound 4

Compound 5

Compound 6

Compound 7

Compound 8

Compound 9

Compound 10

Compound 11

Compound 12

Compound 13

Compound 14

Compound 15

Compound 16

Compound 17

Compound 18

Compound 19

Compound 20

COMPOUNDS SPECIFIC FOR THE HUMAN $\alpha_{1D}$ ADRENERGIC RECEPTOR AND USES THEREOF This application is a continuation of PCT International Application No. PCT/US99/16101, filed Jul. 16, 1999, designating the United States of America, which is a continuation-in-part of U.S. Ser. No. 09/118,323, filed Jul. 17, 1998 now abandoned, the contents of which are hereby incorporated by reference into the present application.

The invention disclosed herein was made with Government support under Small Business Innovation Research (SBIR) Program Grant No. 2 R44 NS33418-02 from the National Institute of Neurological Disorders and Stroke, National Institutes of Health. Accordingly, the U.S. Government has certain rights in the invention.

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the sequence listings and the claims.

BACKGROUND OF THE INVENTION

The designation "$\alpha_{1d}$" is the appellation recently approved by the IUPHAR Nomenclature Committee for the previously designated "$\alpha_{1a}$" cloned subtype as outlined in the Pharmacological Reviews (Hieble, et al., 1995). The designation "$\alpha_{1d}$" is used throughout this application and the supporting tables and figures to refer to this receptor subtype. At the same time, the receptor formerly designated "$\alpha_{1c}$" was renamed "$\alpha_{1a}$". The new nomenclature is used throughout this application. Stable cell lines expressing these receptors are described herein; however, these cell lines were deposited with the American Type Culture Collection (ATCC) under the old nomenclature (infra). In each case, lowercase letters are used to designate cloned receptors (i.e., $\alpha_{1a}$, $\alpha_{1b}$, $\alpha_{1d}$) and uppercase letters are used to designate pharmacologically defined native receptors (i.e., $\alpha_{1A}$, $\alpha_{1B}$, and $\alpha_{1D}$)

α-Adrenergic receptors (McGrath et al., 1989) are specific neuroreceptor proteins both located in the peripheral and central nervous systems and in tissues and organs throughout the body. These receptors are important switches for controlling many physiological functions and, thus, represent important targets for drug development. In fact, many α-adrenergic drugs have been developed over the past 40 years. Examples include clonidine, phenoxybenzamine and prazosin (for treatment of hypertension), naphazoline (a nasal decongestant), and apraclonidine (for treatment of glaucoma). α-Adrenergic drugs can be divided functionally into two distinct classes: agonists (e.g., clonidine and naphazoline), which mimic the receptor activation properties of the endogenous neurotransmitter norepinephrine, and antagonists (e.g., phenoxybenzamine and prazosin), which act to block the effects of norepinephrine. Many of these drugs are effective, but also produce unwanted side effects (e.g., clonidine produces dry mouth and sedation in addition to its antihypertensive effects).

During the past 15 years, a more precise understanding of α-adrenergic receptors and their drugs has evolved through increased scientific scrutiny. Prior to 1977, only one α-adrenergic receptor was known to exist. Between 1977 and 1988, it was accepted by the scientific community that at least two α-adrenergic receptor types—$\alpha_1$ and $\alpha_2$—existed in the central and peripheral nervous systems. Since 1988, new techniques in molecular biology have led to the identification of at least six α-adrenergic receptors which exist throughout the central and peripheral nervous systems: $\alpha_{1A}$ (new nomenclature), $\alpha_{1B}$, $\alpha_{1D}$ (new nomenclature), $\alpha_{2A}$, $\alpha_{2B}$ and $\alpha_{2C}$ (Bylund, D. B., 1992). In many cases, it is not known precisely which physiological responses in the body are controlled by each of these receptors. In addition, current α-adrenergic drugs are not selective for any particular α-adrenergic receptor. Many of these drugs produce untoward side effects that may be attributed to their poor α-adrenergic receptor subtype selectivity.

This invention is directed to compounds which are selective antagonists for cloned human $\alpha_{1d}$ receptors. This invention is also related to the use of these compounds as antihypertensive agents (Deng, F. X. et al., 1996). Experimental evidence presented herein indicates that these compounds, while effective at reducing blood pressure in hypertensive individuals, will be devoid of hypotensive actions in normotensive individuals.

This invention is also related to the use of these compounds for the treatment of Raynaud's disease and for treating bladder instability associated with urinary incontinence (Broten, et al., 1998).

SUMMARY OF THE INVENTION

The invention is directed to a method of inhibiting activation of a human $\alpha_{1d}$ adrenergic receptor which comprises contacting the receptor with a compound so as to inhibit activation of the receptor, wherein the compound binds to the human $\alpha_{1d}$ adrenergic receptor with a binding affinity which is at least ten-fold higher than the binding affinity with which the compound binds to (i) a human $\alpha_{1a}$ adrenergic receptor and (ii) a human $\alpha_{1b}$ adrenergic receptor, and the compound binds to the human $\alpha_{1d}$ adrenergic receptor with a binding affinity which is greater than the binding affinity with which the compound binds to a human 5-$HT_{1a}$ receptor.

This invention is additionally directed to a method of inhibiting activation of a human $\alpha_{1d}$ adrenergic receptor which comprises contacting the receptor with a compound so as to inhibit activation of the receptor, wherein the compound has the structure:

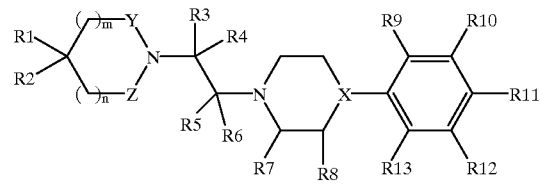

wherein m is an integer from 0 to 2; wherein n is an integer from 0 to 2;

wherein Y is wherein Z is

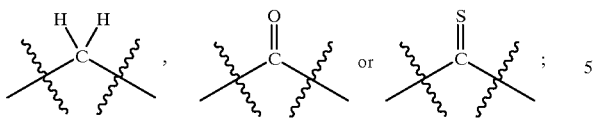

wherein R1 and R2 (i) are independently H, branched or unbranched C$_1$–C$_6$ alkyl or alkoxy, branched or unbranched C$_2$–C$_6$ alkenyl or alkynyl, branched or unbranched C$_1$–C$_6$ hydroxyalkyl, hydroxy, substituted or unsubstituted aryl or aryl-(C$_1$–C$_6$)-alkyl, or substituted or unsubstituted heteroaryl or heteroaryl-(C$_1$–C$_6$)-alkyl, wherein the substituent if present is a halogen, CN, nitro, hydroxy, branched or unbranched C$_1$–C$_6$ alkyl or alkoxy group, or branched or unbranched C$_2$–C$_6$ alkenyl or alkynyl group; or (ii) taken together form a substituted or unsubstituted cycloalkyl ring containing 3–10 carbons, wherein the substituent if present is a branched or unbranched C$_1$–C$_6$ alkyl group or branched or unbranched C$_2$–C$_6$ alkenyl or alkynyl group;

wherein R3 is H, branched or unbranched C$_1$–C$_6$ alkyl, branched or unbranched C$_2$–C$_6$ alkenyl or alkynyl, C$_3$–C$_7$ cycloalkyl, C$_3$–C$_7$ cycloalkylalkyl, aryl, heteroaryl, aryl-(C$_1$–C$_6$)-alkyl, heteroaryl-(C$_1$–C$_6$)-alkyl, substituted C$_1$–C$_6$ alkyl, substituted C$_3$–C$_7$ cycloalkyl, substituted aryl, substituted heteroaryl, substituted aryl-(C$_1$–C$_6$)-alkyl, or substituted heteroaryl-(C$_1$–C$_6$)-alkyl, wherein the substituent if present is a halogen, CN, nitro, C$_1$–C$_6$ alkyl, OR14, SR14, N(R14)$_2$, SO$_2$N(R14)$_2$, CO$_2$R14, SO$_3$R14, N(R14)COR14, CON(R14)$_2$, or N(R14)CON(R14)$_2$;

wherein R4 is H or CH$_3$;

wherein R5 is H, branched or unbranched C$_1$–C$_6$ alkyl, branched or unbranched C$_2$–C$_6$ alkenyl or alkynyl, C$_3$–C$_7$ cycloalkyl, C$_3$–C$_7$ cycloalkylalkyl, aryl, heteroaryl, aryl-(C$_1$–C$_6$)-alkyl, heteroaryl-(C$_1$–C$_6$)-alkyl, substituted C$_1$–C$_6$ alkyl, substituted C$_3$–C$_7$ cycloalkyl, substituted aryl, substituted heteroaryl, substituted aryl-(C$_1$–C$_6$)-alkyl, or substituted heteroaryl-(C$_1$–C$_6$)-alkyl, wherein the substituent if present is a halogen, CN, nitro, C$_1$–C$_6$ alkyl, OR14, SR14, N(R14)$_2$, SO$_2$N(R14)$_2$, CO$_2$R14, SO$_3$R14, N(R14)COR14, CON(R14)$_2$, or N(R14)CON(R14)$_2$;

wherein R6 is H, branched or unbranched C$_1$–C$_6$ alkyl, branched or unbranched C$_2$–C$_6$ alkenyl or alkynyl, C$_3$–C$_7$ cycloalkyl, C$_3$–C$_7$ cycloalkylalkyl, aryl, heteroaryl, aryl-(C$_1$–C$_6$)-alkyl, heteroaryl-(C$_1$–C$_6$)-alkyl, substituted C$_1$–C$_6$ alkyl, substituted C$_3$–C$_7$ cycloalkyl, substituted aryl, substituted heteroaryl, substituted aryl-(C$_1$–C$_6$)-alkyl, or substituted heteroaryl-(C$_3$–C$_6$)-alkyl, wherein the substituent if present is a halogen, CN, nitro, C$_1$–C$_6$ alkyl, OR14, SR14, N(R14)$_2$, SO$_2$N(R14)$_2$, C$_{02}$R14, SO$_3$R14, N(R14)COR14, CON(R14)$_2$, or N(R14)CON(R14)$_2$;

wherein R7 is H, branched or unbranched C$_1$–C$_6$ alkyl, branched or unbranched C$_2$–C$_6$ alkenyl or alkynyl, C$_3$–C$_7$ cycloalkyl, aryl, aryl-(C$_1$–C$_6$)-alkyl, CO$_2$R14, CON(R14)$_2$, substituted C$_1$–C$_6$ alkyl, substituted aryl, wherein the substituent is N(R14)$_2$, halogen, OR14 or SR14;

wherein R8 is H or CH$_3$;

wherein R9 is H, F, Cl, Br, branched or unbranched C$_1$–C$_6$ alkyl or alkoxy, CN; wherein R10 is H or F; wherein R11 is H, F, Cl, Br, I, CN, branched or unbranched C$_1$–C$_6$ alkyl or alkoxy; wherein R12 is H, F, Cl, CN, branched or unbranched C$_1$–C$_6$ alkyl or alkoxy; wherein R13 is H or F; wherein X is N or CH; with the proviso that when R11 and R12 are each H, then R9 is F;

and wherein R14 is independently H or branched or unbranched C$_1$–C$_6$ alkyl.

This invention is additionally directed to a compound having the structure:

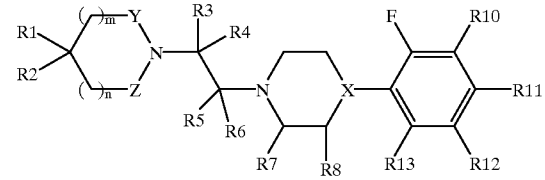

wherein n is an integer from 0 to 2; wherein m is an integer from 0 to 2;

wherein Y is

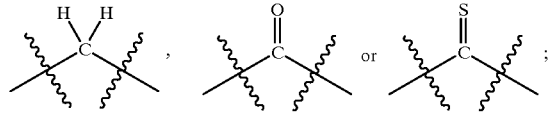

wherein Z is

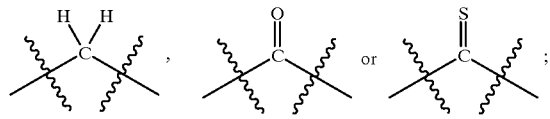

wherein R1 and R2 (i) are independently H, branched or unbranched C$_1$–C$_6$ alkyl or alkoxy, branched or unbranched C$_2$–C$_6$, alkenyl or alkynyl, branched or unbranched C$_1$–C$_6$ hydroxyalkyl, hydroxy, substituted or unsubstituted aryl or aryl-(C$_1$–C$_6$)-alkyl, or substituted or unsubstituted heteroaryl or heteroaryl-(C$_1$–C$_6$)-alkyl, wherein the substituent if present is a halogen, CN, nitro, hydroxy, branched or unbranched C$_1$–C$_6$ alkyl or alkoxy group, or branched or unbranched C$_2$–C$_6$ alkenyl or alkynyl group; or (ii) taken together form a substituted or unsubstituted cycloalkyl ring containing 3–10 carbons, wherein the substituent if present is a branched or unbranched C$_1$–C$_6$ alkyl group or branched or unbranched C$_2$–C$_6$ alkenyl or alkynyl group;

wherein R3 is H, branched or unbranched C$_1$–C$_6$ alkyl, branched or unbranched C$_2$–C$_6$ alkenyl or alkynyl, C$_3$–C$_7$ cycloalkyl, C$_3$–C$_7$ cycloalkylalkyl, aryl, heteroaryl, aryl-(C$_1$–C$_6$)-alkyl, heteroaryl-(C$_1$–C$_6$)-alkyl, substituted C$_1$–C$_6$ alkyl, substituted C$_3$–C$_7$ cycloalkyl, substituted aryl, substituted heteroaryl, substituted aryl-(C$_1$–C$_6$)-alkyl, or substituted heteroaryl-(C$_1$–C$_6$)-alkyl, wherein the substituent if present is a halogen, CN, nitro, C$_1$–C$_6$ alkyl, OR14, SR14, N(R14)$_2$, SO$_2$N(R14)$_2$, CO$_2$R14, SO$_3$R14, N(R14)COR14, CON(R14)$_2$, or N(R14)CON(R14)$_2$;

wherein R4 is H or CH$_3$;

wherein R5 is H, branched or unbranched C$_1$–C$_6$ alkyl, branched or unbranched C$_2$–C$_6$ alkenyl or alkynyl, $C_3-C_7$ cycloalkyl, $C_3-C_7$ cycloalkylalkyl, aryl, heteroaryl, aryl-$(C_1-C_6)$-alkyl, heteroaryl-$(C_1-C_6)$-alkyl, substituted $C_1-C_6$ alkyl, substituted $C_3-C_7$ cycloalkyl, substituted aryl, substituted heteroaryl, substituted aryl-$(C_1-C_6)$-alkyl, or substituted heteroaryl-$(C_1-C_6)$-alkyl, wherein the substituent if present is a halogen, CN, nitro, $C_1-C_6$ alkyl, OR14, SR14, $N(R14)_2$, $SO_2N(R14)_2$, $CO_2R14$, $SO_3R14$, $N(R14)COR14$, $CON(R14)_2$, or $N(R14)CON(R14)_2$;

wherein R6 is H, branched or unbranched $C_1-C_6$ alkyl, branched or unbranched $C_2-C_6$ alkenyl or alkynyl, $C_3-C_7$ cycloalkyl, $C_3-C_7$ cycloalkylalkyl, aryl, heteroaryl, aryl-$(C_1-C_6)$-alkyl, heteroaryl-$(C_1-C_6)$-alkyl, substituted $C_1-C_6$ alkyl, substituted $C_3-C_7$ cycloalkyl, substituted aryl, substituted heteroaryl, substituted aryl-$(C_1-C_6)$-alkyl, or substituted heteroaryl-$(C_1-C_6)$-alkyl, wherein the substituent if present is a halogen, CN, nitro, $C_1-C_6$ alkyl, OR14, SR14, $N(R14)_2$ $SO_2N(R14)_2$, $CO_2R14$, $SO_3R14$, $N(R14)COR14$, $CON(R14)_2$, or $N(R14)CON(R14)_2$;

wherein R7 is H, branched or unbranched $C_1-C_6$ alkyl, branched or unbranched $C_2-C_6$ alkenyl or alkynyl, $C_3-C_7$ cycloalkyl, aryl, aryl-$(C_1-C_6)$-alkyl, $CO_2R14$, $CON(R14)_2$, substituted $C_1-C_6$ alkyl, substituted aryl, wherein the substituent is $N(R14)_2$, halogen, OR14 or SR14;

wherein R8 is H or $CH_3$;

wherein R10 is H or F; wherein R11 is H, F, Cl, Br, I, CN, branched or unbranched $C_1-C_6$ alkyl or alkoxy; wherein R12 is H, F, Cl, CN, branched or unbranched $C_2-C_6$ alkyl or alkoxy; wherein R13 is H or F; wherein X is N or CH; and wherein R14 is independently H or branched or unbranched $C_1-C_6$ alkyl.

This invention is additionally directed towards a pharmaceutical composition comprising a therapeutically effective amount of the compound of this invention and a pharmaceutically acceptable carrier.

This invention is additionally directed towards a pharmaceutical composition obtained by combining a therapeutically effective amount of a compound of this invention and a pharmaceutically acceptable carrier.

This invention is additionally directed towards a process for making a pharmaceutical composition comprising combining a therapeutically effective amount of a compound of this invention and a pharmaceutically acceptable carrier.

This invention is additionally directed towards a process of making a compound with structure:

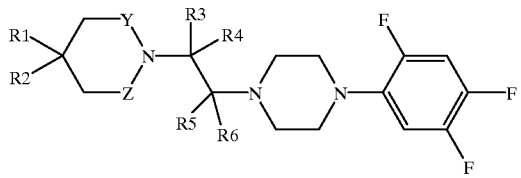

which comprises reacting a compound with structure:

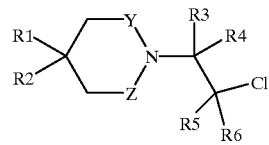

with a compound

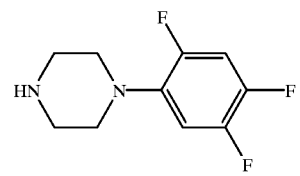

to form the compound,
wherein Y is

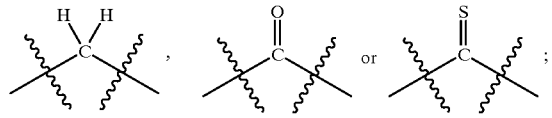

wherein Z is

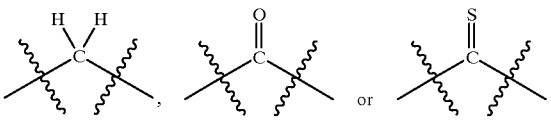

wherein R1 and R2 (i) are independently H, branched or unbranched $C_1-C_6$ alkyl or alkoxy, branched or unbranched $C_2-C_6$ alkenyl or alkynyl, branched or unbranched $C_1-C_6$ hydroxyalkyl, hydroxy, substituted or unsubstituted aryl or aryl-$(C_1-C_6)$-alkyl, or substituted or unsubstituted heteroaryl or heteroaryl-$(C_1-C_6)$-alkyl, wherein the substituent if present is a halogen, CN, nitro, hydroxy, branched or unbranched $C_1-C_6$ alkyl or alkoxy group, or branched or unbranched $C_2-C_6$ alkenyl or alkynyl group; or (ii) taken together form a substituted or unsubstituted cycloalkyl ring containing 3–10 carbons, wherein the substituent if present is a branched or unbranched $C_1-C_6$ alkyl group or branched or unbranched $C_2-C_6$ alkenyl or alkynyl group;

wherein R3 is H, branched or unbranched $C_1-C_6$ alkyl, branched or unbranched $C_2-C_6$ alkenyl or alkynyl, $C_3-C_7$ cycloalkyl, $C_3-C_7$ cycloalkylalkyl, aryl, heteroaryl, aryl-$(C_1-C_6)$-alkyl, heteroaryl-$(C_1-C_6)$-alkyl, substituted $C_1-C_6$ alkyl, substituted $C_3-C_7$ cycloalkyl, substituted aryl, substituted heteroaryl, substituted aryl-$(C_1-C_6)$-alkyl, or substituted heteroaryl-$(C_1-C_6)$-alkyl, wherein the substituent if present is a halogen, CN, nitro, $C_1-C_6$ alkyl, OR14, SR14, $N(R14)_2$, $SO_2N(R14)_2$, $CO_2R14$, $SO_3R14$, $N(R14)COR14$, $CON(R14)_2$, or $N(R14)CON(R14)_2$;

wherein R4 is H or $CH_3$;

wherein R5 is H, branched or unbranched $C_1-C_6$ alkyl, branched or unbranched $C_2-C_6$ alkenyl or alkynyl, $C_3-C_7$ cycloalkyl, $C_3-C_7$ cycloalkylalkyl, aryl, heteroaryl, aryl-$(C_1-C_6)$-alkyl, heteroaryl-$(C_1-C_6)$-alkyl, substituted $C_1-C_6$ alkyl, substituted $C_3-C_7$ cycloalkyl, substituted aryl, substituted heteroaryl, substituted aryl-$(C_1-C_6)$-alkyl, or substituted heteroaryl-$(C_1-C_6)$-alkyl, wherein the substituent if present is a halogen, CN, nitro, $C_1-C_6$ alkyl, OR14, SR14, $N(R14)_2$, $SO_2N(R14)_2$, $CO_2R14$, $SO_3R14$, $N(R14)COR14$, $CON(R14)_2$, or $N(R14)CON(R14)_2$;

wherein R6 is H, branched or unbranched $C_1-C_6$ alkyl, branched or unbranched $C_2-C_6$ alkenyl or alkynyl, $C_3$–$C_7$ cycloalkyl, $C_3$–$C_7$ cycloalkylalkyl, aryl, heteroaryl, aryl-($C_1$–$C_6$)-alkyl, heteroaryl-($C_1$–$C_6$)-alkyl, substituted $C_1$–$C_6$ alkyl, substituted $C_3$–$C_7$ cycloalkyl, substituted aryl, substituted heteroaryl, substituted aryl-($C_1$–$C_6$)-alkyl, or substituted heteroaryl-($C_1$–$C_6$)-alkyl, wherein the substituent if present is a halogen, CN, nitro, $C_1$–$C_6$ alkyl, OR14, SR14, N(R14)$_2$, SO$_2$N(R14)$_2$ CO$_2$R14, SO$_3$R14, N(R14)COR14, CON(R14)$_2$, or N(R14)CON(R14)$_2$; and wherein R14 is independently H or branched or unbranched $C_1$–$C_6$ alkyl.

This invention is additionally directed towards a method of treating a subject afflicted with a disease which is susceptible to treatment by antagonism of the human $\alpha_{1d}$ adrenergic receptor which comprises administering to the subject an amount of the compound of this invention effective to treat the disease.

This invention is additionally directed towards a method of treating a subject afflicted with hypertension which comprises administering to the subject an amount of the compound of this invention effective to treat hypertension.

This invention is directed towards a method of treating a subject afflicted with Raynaud's disease which comprises administering to the subject an amount of the compound of this invention effective to treat Raynaud's disease.

This invention is directed towards a method of treating a subject afflicted with urinary incontinence which comprises administering to the subject an amount of the compound of this invention effective to treat urinary incontinence.

This invention is directed towards a method of treating urinary incontinence in a subject which comprises administering to the subject a therapeutically effective amount of a $\alpha_{1d}$ antagonist which binds to the human $\alpha_{1d}$ adrenergic receptor with a binding affinity which is at least ten-fold higher than the binding affinity with which the $\alpha_{1d}$ antagonist binds to (i) a human $\alpha_{1a}$ adrenergic receptor and (ii) a human $\alpha_{1b}$ adrenergic receptor, and the $\alpha_{1d}$ antagonist binds to the human $\alpha_{1d}$ adrenergic receptor with a binding affinity which is greater than the binding affinity with which the $\alpha_{1d}$ antagonist binds to a human 5-$HT_{1a}$ receptor.

DETAILED DESCRIPTION OF THE INVENTION

Figure 1A:
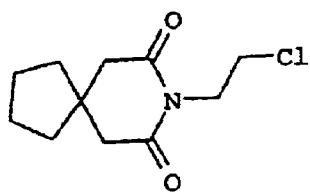
FIGS. 1A–1C FIGS. 1A–1C show the structures of the compounds described herein in the Examples.
Figure 1A:
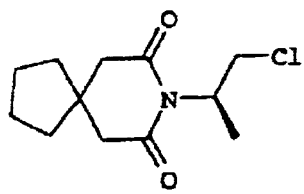
Figure 1A:
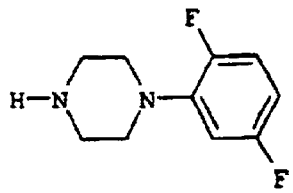
Figure 1A:
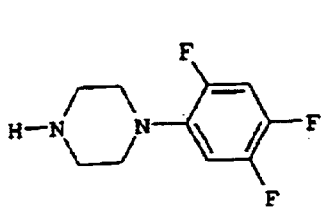
Figure 1A:
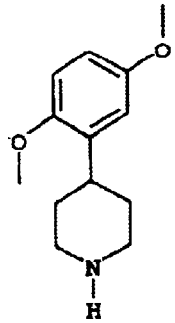
Figure 1A:
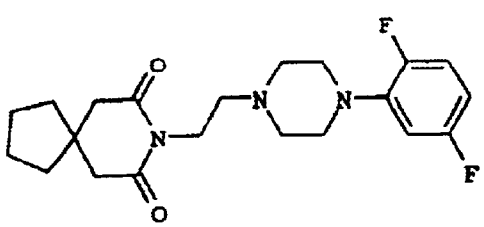
Figure 1A:
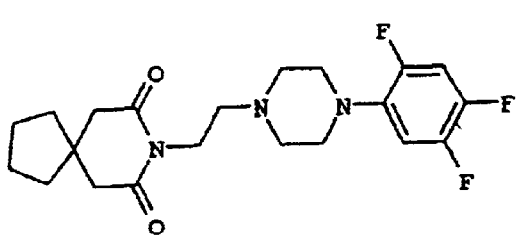
Figure 1A:
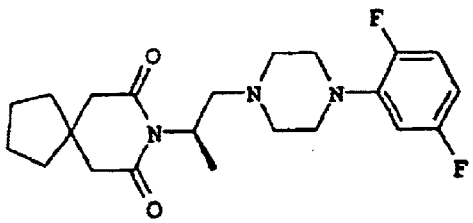
Figure 1A:
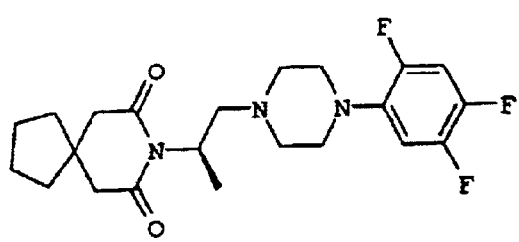
Figure 1A:
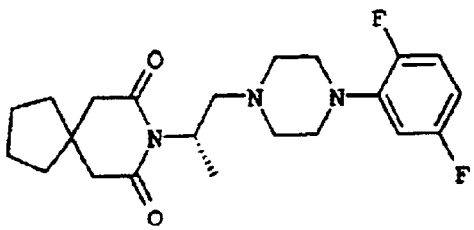
Figure 1B:
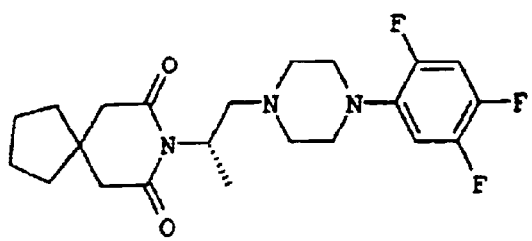
Figure 1B:
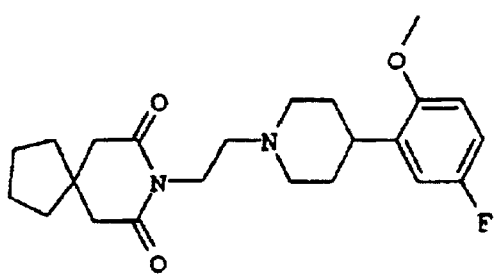
Figure 1B:
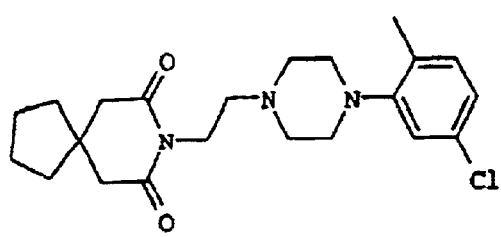
Figure 1B:
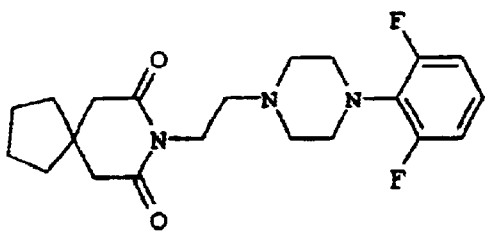
Figure 1B:
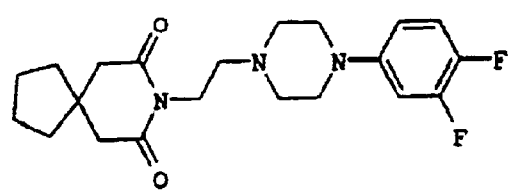
Figure 1B:
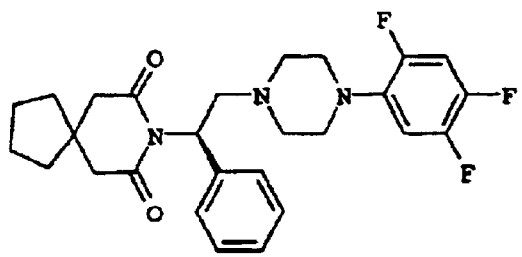
Figure 1B:
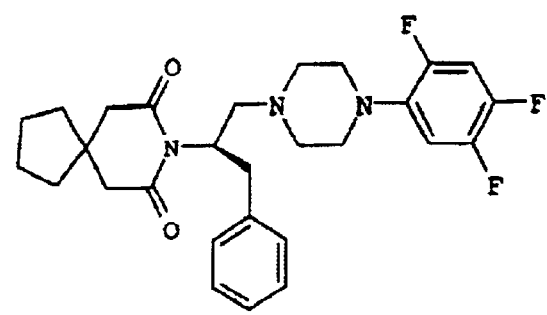
Figure 1B:
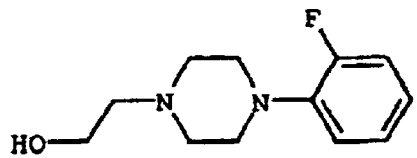
Figure 1C:
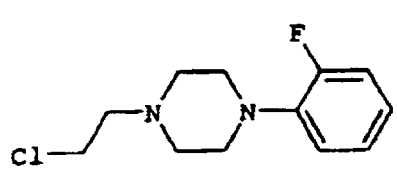
Figure 1C:
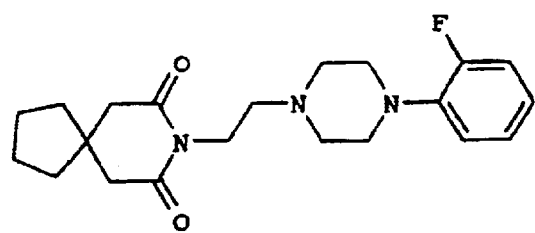

This invention is directed towards a method of inhibiting activation of a human $\alpha_{1d}$ adrenergic receptor which comprises contacting the receptor with a compound so as to inhibit activation of the receptor, wherein the compound binds to the human $\alpha_{1d}$ adrenergic receptor with a binding affinity which is at least ten-fold higher than the binding affinity with which the compound binds to (i) a human $\alpha_{1a}$ adrenergic receptor and (ii) a human $\alpha_{1b}$ adrenergic receptor, and the compound binds to the human $\alpha_{1d}$ adrenergic receptor with a binding affinity which is greater than the binding affinity with which the compound binds to a human 5-$HT_{1a}$ receptor.

In one embodiment, the compound binds to the human $\alpha_{1d}$ adrenergic receptor with a binding affinity which is at least 25-fold higher than the binding affinity with which the compound binds to (i) the human $\alpha_{1a}$ adrenergic receptor and (ii) the human $\alpha_{1b}$ adrenergic receptor, and the compound binds to the human $\alpha_{1d}$ adrenergic receptor with a binding affinity which is at least ten-fold higher than the binding affinity with which the compound binds to the human 5-$HT_{1a}$ receptor.

In another embodiment, the compound binds to the human $\alpha_{1d}$ adrenergic receptor with a binding affinity which is at least 25-fold higher than the binding affinity with which the compound binds to (i) the human $\alpha_{1a}$ adrenergic receptor, (ii) the human $\alpha_{1b}$ adrenergic receptor, and (iii) the human 5-$HT_{1a}$ receptor.

In another embodiment, the compound binds to the human $\alpha_{1d}$ adrenergic receptor with a binding affinity which is at least 100-fold higher than the binding affinity with which the compound binds to (i) the human $\alpha_{1a}$ adrenergic receptor, (ii) the human $\alpha_{1b}$ adrenergic receptor, and (iii) the human 5-$HT_{1a}$ receptor.

This invention is additionally directed to a method of inhibiting activation of a human $\alpha_{1d}$ adrenergic receptor which comprises contacting the receptor with a compound so as to inhibit activation of the receptor, wherein the compound has the structure:

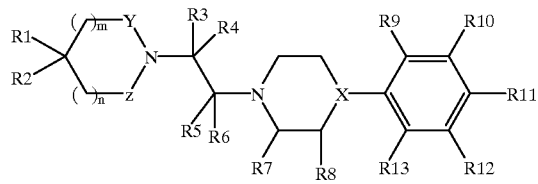

wherein m is an integer from 0 to 2; wherein n is an integer from 0 to 2;
wherein Y is

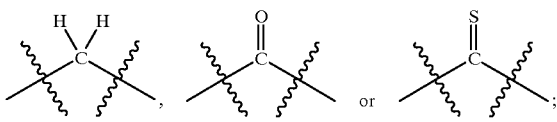

wherein Z is

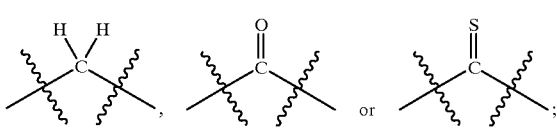

wherein R1 and R2 (i) are independently H, branched or unbranched $C_1$–$C_6$ alkyl or alkoxy, branched or unbranched $C_2$–$C_6$ alkenyl or alkynyl, branched or unbranched $C_1$–$C_6$ hydroxyalkyl, hydroxy, substituted or unsubstituted aryl or aryl-($C_1$–$C_6$)-alkyl, or substituted or unsubstituted heteroaryl or heteroaryl-($C_1$–$C_6$)-alkyl, wherein the substituent if present is a halogen, CN, nitro, hydroxy, branched or unbranched $C_1$–$C_6$ alkyl or alkoxy group, or branched or unbranched $C_2$–$C_6$ alkenyl or alkynyl group; or (ii) taken together form a substituted or unsubstituted cycloalkyl ring containing 3–10 carbons, wherein the substituent if present is a branched or unbranched $C_1$–$C_6$ alkyl group or branched or unbranched $C_2$–$C_6$ alkenyl or alkynyl group;

wherein R3 is H, branched or unbranched $C_1$–$C_6$ alkyl, branched or unbranched $C_2$–$C_6$ alkenyl or alkynyl, $C_3$–$C_7$ cycloalkyl, $C_3$–$C_7$ cycloalkylalkyl, aryl, heteroaryl, aryl-($C_1$–$C_6$)-alkyl, heteroaryl-($C_1$–$C_6$)-alkyl, substituted $C_1$–$C_6$ alkyl, substituted $C_3$–$C_7$ cycloalkyl, substituted aryl, substituted heteroaryl, substituted aryl-($C_1$–$C_6$)-alkyl, or substituted heteroaryl-($C_1$–$C_6$)-alkyl, wherein the substituent if present is a halogen, CN, nitro, $C_1$–$C_6$ alkyl, OR14, SR14, N(R14)$_2$, SO$_2$N(R14)$_2$, CO$_2$R14, SO$_3$R14, N(R14)COR14, CON(R14)$_2$, or N(R14)CON(R14)$_2$;

wherein R4 is H or $CH_3$;

wherein R5 is H, branched or unbranched $C_1$–$C_6$ alkyl, branched or unbranched $C_2$–$C_6$ alkenyl or alkynyl, $C_3$–$C_7$ cycloalkyl, $C_3$–$C_7$ cycloalkylalkyl, aryl, heteroaryl, aryl-($C_1$–$C_6$)-alkyl, heteroaryl-($C_1$–$C_6$)-alkyl, substituted $C_1$–$C_6$ alkyl, substituted $C_3$–$C_7$ cycloalkyl, substituted aryl, substituted heteroaryl, substituted aryl-($C_1$–$C_6$)-alkyl, or substituted heteroaryl-($C_1$–$C_6$)-alkyl, wherein the substituent if present is a halogen, CN, nitro, $C_1$–$C_6$ alkyl, OR14, SR14, N(R14)$_2$, SO$_2$N(R14)$_2$, CO$_2$R14, SO$_3$R14, N(R14)COR14, CON(R14)$_2$, or N(R14)CON(R14)$_2$;

wherein R6 is H, branched or unbranched $C_1$–$C_6$ alkyl, branched or unbranched $C_2$–$C_6$ alkenyl or alkynyl, $C_3$–$C_7$ cycloalkyl, $C_3$–$C_7$ cycloalkylalkyl, aryl, heteroaryl, aryl-($C_1$–$C_6$)-alkyl, heteroaryl-($C_1$–$C_6$)-alkyl, substituted $C_1$–$C_6$ alkyl, substituted $C_3$–$C_7$ cycloalkyl, substituted aryl, substituted heteroaryl, substituted aryl-($C_1$–$C_6$)-alkyl, or substituted heteroaryl-($C_1$–$C_6$)-alkyl, wherein the substituent if present is a halogen, CN, nitro, $C_1$–$C_6$ alkyl, OR14, SR14, N(R14)$_2$, SO$_2$N(R14)$_2$, CO$_2$R14, SO$_3$R14, N(R14)COR14, CON(R14)$_2$, or N(R14)CON(R14)$_2$;

wherein R7 is H, branched or unbranched $C_1$–$C_6$ alkyl, branched or unbranched $C_2$–$C_6$ alkenyl or alkynyl, $C_3$–$C_7$ cycloalkyl, aryl, aryl-($C_1$–$C_6$)-alkyl, CO$_2$R14, CON(R14)$_2$, substituted $C_1$–$C_6$ alkyl, substituted aryl, wherein the substituent is N(R14)$_2$, halogen, OR14 or SR14;

wherein R8 is H or $CH_3$;

wherein R9 is H, F, Cl, Br, branched or unbranched $C_1$–$C_6$ alkyl or alkoxy, CN; wherein R10 is H or F; wherein R11 is H, F, Cl, Br, I, CN, branched or unbranched $C_1$–$C_6$ alkyl or alkoxy; wherein R12 is H, F, Cl, CN, branched or unbranched $C_1$–$C_6$ alkyl or alkoxy; wherein R13 is H or F; wherein X is N or CH; with the proviso that when R11 and R12 are each H, then R9 is F;

and wherein R14 is independently H or branched or unbranched $C_1$–$C_6$ alkyl.

In one embodiment, the compound has the structure:

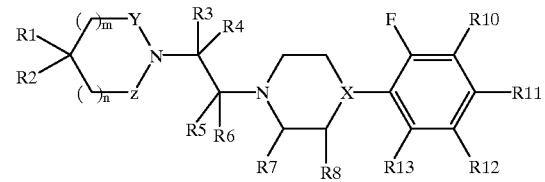

In another embodiment, the compound has the structure:

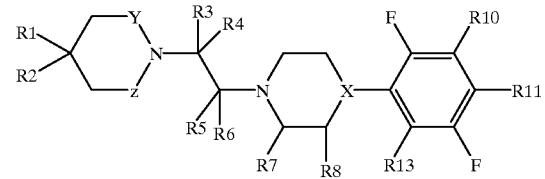

In another embodiment, the compound has the structure:

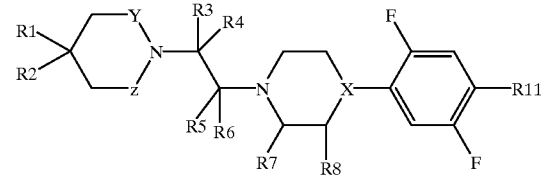

In another embodiment, the compound has the structure:

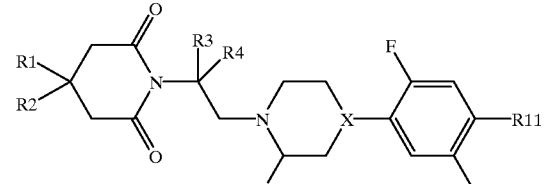

In another embodiment, the compound has the structure:

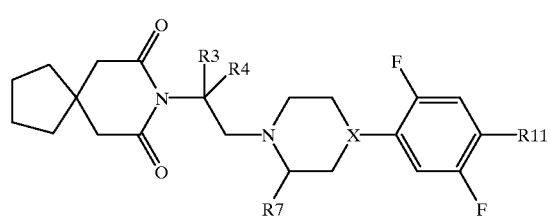

In another embodiment, the compound has the structure:

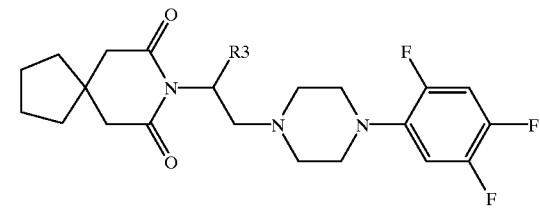

In another embodiment, the compound has the structure:

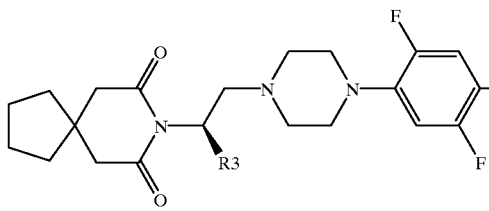

This invention is additionally directed to a compound having the structure:

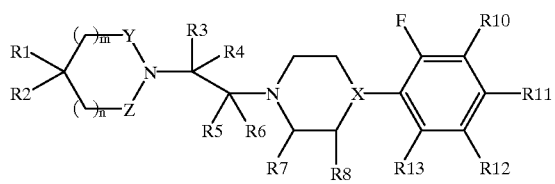

wherein n is an integer from 0 to 2; wherein m is an integer from 0 to 2;
wherein Y is

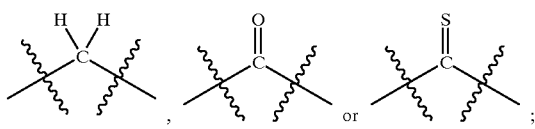

wherein Z is

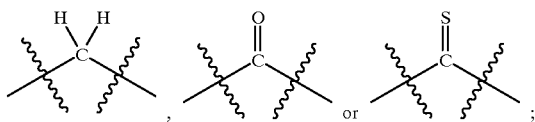

wherein R1 and R2 (i) are independently H, branched or unbranched $C_1$–$C_6$ alkyl or alkoxy, branched or unbranched $C_2$–$C_6$ alkenyl or alkynyl, branched or unbranched $C_1$–$C_6$ hydroxyalkyl, hydroxy, substituted or unsubstituted aryl or aryl-($C_1$–$C_6$)-alkyl, or substituted or unsubstituted heteroaryl or heteroaryl-($C_1$–$C_6$)-alkyl, wherein the substituent if present is a halogen, CN, nitro, hydroxy, branched or unbranched $C_1$–$C_6$ alkyl or alkoxy group, or branched or unbranched $C_2$–$C_6$ alkenyl or alkynyl group; or (ii) taken together form a substituted or unsubstituted cycloalkyl ring containing 3–10 carbons, wherein the substituent if present is a branched or unbranched $C_1$–$C_6$ alkyl group or branched or unbranched $C_2$–$C_6$ alkenyl or alkynyl group;

wherein R3 is H, branched or unbranched $C_1$–$C_6$ alkyl, branched or unbranched $C_2$–$C_6$ alkenyl or alkynyl, $C_3$–$C_6$ cycloalkyl, $C_3$–$C_7$ cycloalkylalkyl, aryl, heteroaryl, aryl-($C_1$–$C_6$)-alkyl, heteroaryl-($C_1$–$C_6$)-alkyl, substituted $C_1$–$C_6$ alkyl, substituted $C_3$–$C_7$ cycloalkyl, substituted aryl, substituted heteroaryl, substituted aryl-($C_1$–$C_6$)-alkyl, or substituted heteroaryl-($C_1$–$C_6$)-alkyl, wherein the substituent if present is a halogen, CN, nitro, $C_1$–$C_6$ alkyl, OR14, SR14, N(R14)$_2$, SO$_2$N(R14)$_2$, CO$_2$R14, SO$_3$R14, N(R14)COR14, CON(R14)$_2$, or N(R14)CON(R14)$_2$;

wherein R4 is H or CH$_3$;

wherein R5 is H, branched or unbranched $C_1$–$C_6$ alkyl, branched or unbranched $C_2$–$C_6$ alkenyl or alkynyl, $C_3$–$C_7$ cycloalkyl, $C_3$–$C_7$ cycloalkylalkyl, aryl, heteroaryl, aryl-($C_1$–$C_6$)-alkyl, heteroaryl-($C_1$–$C_6$)-alkyl, substituted $C_1$–$C_6$ alkyl, substituted $C_3$–$C_7$ cycloalkyl, substituted aryl, substituted heteroaryl, substituted aryl-($C_1$–$C_6$)-alkyl, or substituted heteroaryl-($C_1$–$C_6$)-alkyl, wherein the substituent if present is a halogen, CN, nitro, $C_1$–$C_6$ alkyl, OR14, SR14, N(R14)$_2$, SO$_2$N(R14)$_2$, CO$_2$R14, SO$_3$R14, N(R14)COR14, CON(R14)$_2$, or N(R14)CON(R14)$_2$;

wherein R6 is H, branched or unbranched $C_1$–$C_6$ alkyl, branched or unbranched $C_2$–$C_6$ alkenyl or alkynyl, $C_3$–$C_7$ cycloalkyl, $C_3$–$C_7$ cycloalkylalkyl, aryl, heteroaryl, aryl-($C_1$–$C_6$)-alkyl, heteroaryl-($C_1$–$C_6$)-alkyl, substituted $C_1$–$C_6$ alkyl, substituted $C_3$–$C_7$ cycloalkyl, substituted aryl, substituted heteroaryl, substituted aryl-($C_1$–$C_6$)-alkyl, or substituted heteroaryl-($C_1$–$C_6$)-alkyl, wherein the substituent if present is a halogen, CN, nitro, $C_1$–$C_6$ alkyl, OR14, SR14, N(R14)$_2$, SO$_2$N(R14)$_2$, CO$_2$R14, SO$_3$R14, N(R14)COR14, CON(R14)$_2$, or N(R14)CON(R14)$_2$;

wherein R7 is H, branched or unbranched $C_1$–$C_6$ alkyl, branched or unbranched $C_2$–$C_6$ alkenyl or alkynyl, $C_3$–$C_7$ cycloalkyl, aryl, aryl-($C_1$–$C_6$)-alkyl, CO$_2$R14, CON(R14)$_2$, substituted $C_1$–$C_6$ alkyl, substituted aryl, wherein the substituent is N(R14)$_2$, halogen, OR14 or SR14;

wherein R8 is H or CH$_3$;

wherein R10 is H or F; wherein R11 is H, F, Cl, Br, I, CN, branched or unbranched $C_1$–$C_6$ alkyl or alkoxy; wherein R12 is H, F, Cl, CN, branched or unbranched $C_1$–$C_6$ alkyl or alkoxy; wherein R13 is H or F; wherein X is N or CH; and wherein R14 is independently H or branched or unbranched $C_1$–$C_6$ alkyl.

In one embodiment, the compound has the structure:

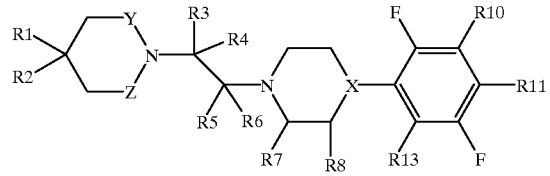

In another embodiment, the compound has the structure:

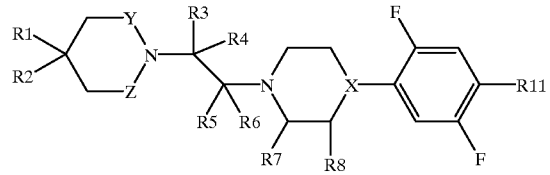

In another embodiment, the compound has the structure:

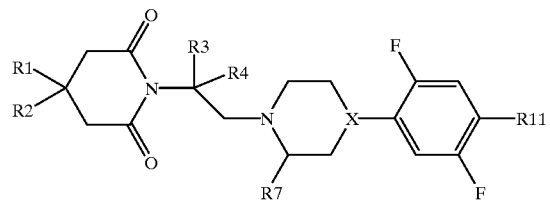

In another embodiment, the compound has the structure:

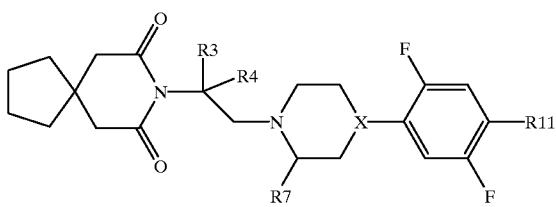

In another embodiment, the compound has the structure:
In another embodiment, the compound has the structure:

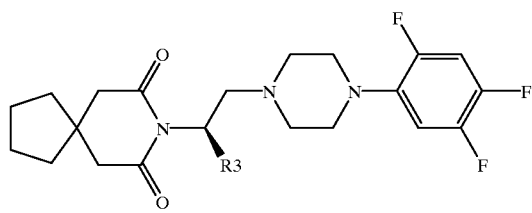

The compounds of the present invention may be present as single enantiomers, diasteriomers, or cis or trans isomers; or two or more of the compounds may be present to form a mixture of enantiomers, diasteriomers, or isomers, including a racemic mixture.

The invention also provides for the (−) and (+) enantiomers of all compounds of the subject application described herein.

The invention further provides for the cis, trans, erythro, and threo isomers of all of the compounds of the subject application described herein. It is noted herein that the terms "cis", "trans", "erythro", and "threo" correspond to relative stereochemistry, as determined, for example, by NOE (Nuclear Overhauser Effect) experiments.

The compounds of the present invention are preferably at least 80% pure, more preferably at least 90% pure, and most preferably at least 95% pure.

In the present invention, the term aryl is used to include phenyl, benzyl, benzoyl, or naphthyl, and the term heteroaryl is used to include pyrazinyl, pyrrolyl, furanyl, thiophenyl, pyridyl, imidazolyl, imidazolinyl, indolyl, benzimidazolyl, benzfuranyl, pyrimidyl, benzothiophenyl, isoquinolyl, or quinolyl. The term aryl-($C_1$-$C_6$)-alkyl is used to designate an $C_1$-$C_6$ alkyl chain substituted with an aryl group and the term heteroaryl-($C_1$-$C_6$)-alkyl is used to designate a $C_1$-$C_6$ alkyl chain substituted with a heteroaryl group.

Abbreviations used in the specification, in particular the Schemes and Examples, are as follows:

| | |
|---|---|
| TFA | trifluoroacetic acid |
| HCl | hydrochloric acid |
| $C_5H_5N$ | pyridine |
| $SOCl_2$ | thionyl chloride |
| $LiAlH_4$ | lithium aluminum hydride |
| BuOH | butyl alcohol |
| $Na_2CO_3$ | sodium carbonate |
| $NH_4Cl$ | ammonium chloride |
| $H_2$ | hydrogen |
| Pd/C | palladium on charcoal |
| Pd | palladium |
| dba | dibenzylideneacetone |
| BINAP | 2,2'-bis(diphenylphosphino)-1,1'-binaphthyl |

The invention is additionally directed towards a pharmaceutical composition comprising a therapeutically effective amount of the compound of the invention and a pharmaceutically acceptable carrier.

In one embodiment, the amount of the compound is an amount from about 0.01 mg to about 800 mg.

In another embodiment, the amount of the compound is from about 0.1 mg to about 300 mg.

In another embodiment, the amount of the compound is from about 1 mg to about 20 mg.

In another embodiment, the carrier is a liquid.

In another embodiment, the carrier is a solid.

In another embodiment, the carrier is a gel.

The invention is additionally directed towards a pharmaceutical composition obtained by combining a therapeutically effective amount of a compound of the invention and a pharmaceutically acceptable carrier.

The invention is additionally directed towards a process for making a pharmaceutical composition comprising combining a therapeutically effective amount of a compound of the invention and a pharmaceutically acceptable carrier.

In the subject invention, a "therapeutically effective amount" is any amount of a compound which, when administered to a subject suffering from a disease against which the compounds are effective, causes reduction, remission, or regression of the disease or reduction of or relief from symptoms of the disease. In the practice of this invention, the "pharmaceutically acceptable carrier" is any physiological carrier known to those of ordinary skill in the art useful in formulating pharmaceutical compositions.

In one embodiment the pharmaceutical carrier may be a liquid and the pharmaceutical composition would be in the form of a solution. In another embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and-polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The compound can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The compound can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular compound in use, the strength of the preparation, the mode of administration, and the advancement of the disease condition. Additional factors depending on the particular subject being treated will result in a need to adjust dosages, including subject age, weight, gender, diet, and time of administration.

Included in this invention are pharmaceutically acceptable salts and complexes of all of the compounds described herein. The salts include but are not limited to the following acids and bases: Inorganic acids which include hydrochloric acid, hydrofluoric acid, hydrobromic acid, hydroiodic acid, sulfuric acid, and boric acid; organic acids which include acetic acid, trifluoroacetic acid, formic acid, oxalic acid, malonic acid, succinic acid, fumaric acid, tartaric acid, maleic acid, citric acid, methanesulfonic acid, trifluoromethanesulfonic acid, benzoic acid, glycolic acid, lactic acid, and mandelic acid; inorganic bases which include ammonia and hydrazine; and organic bases which include methylamine, ethylamine, hydroxyethylamine, propylamine, dimethylamine, diethylamine, trimethylamine, triethylamine, ethyleneamine, hydroxyethylamine, morpholine, piperazine, and guanidine. This invention further provides for the hydrates and polymorphs of all of the compounds described herein.

This invention further provides for metabolites of the compounds of the present invention. The in vivo activities and mechanisms of action of numerous enzymes responsible for the generation of metabolites of pharmaceutical compounds are well-known in the art. For example, ethers may be modified to alcohols, esters may be modified by esterases, or amides may be modified by amidases and peptidases.

This invention further provides a prodrug of the compounds disclosed herein. Knowledge of metabolic activities allows the design of prodrug compounds which, when administered to a subject, such as a human, are expected to yield metabolites which include the compounds of the present invention.

This invention is additionally directed to a process of making a compound with structure:

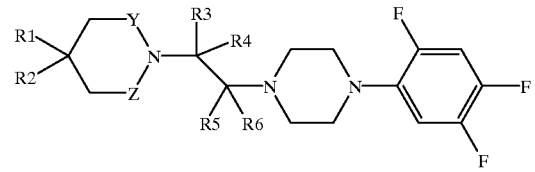

which comprises reacting a compound with structure:

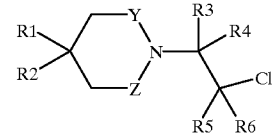

with a compound

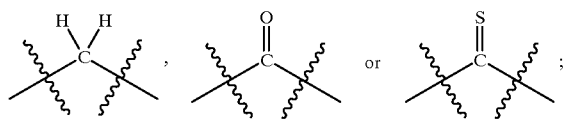

to form the compound,
wherein Y is

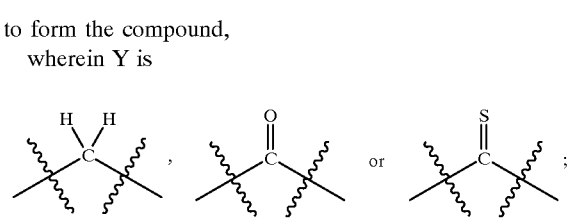

wherein Z is

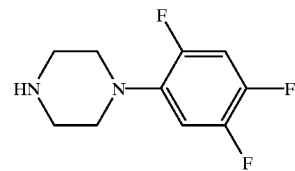

wherein R1 and R2 (i) are independently H, branched or unbranched $C_1-C_6$ alkyl or alkoxy, branched or unbranched $C_2-C_6$ alkenyl or alkynyl, branched or unbranched $C_1-C_6$ hydroxyalkyl, hydroxy, substituted or unsubstituted aryl or aryl-($C_1-C_6$)-alkyl, or substituted or unsubstituted heteroaryl or heteroaryl-($C_1-C_6$)-alkyl, wherein the substituent if present is a halogen, CN, nitro, hydroxy, branched or unbranched $C_1$–$C_6$ alkyl or alkoxy group, or branched or unbranched $C_2$–$C_6$ alkenyl or alkynyl group; or (ii) taken together form a substituted or unsubstituted cycloalkyl ring containing 3–10 carbons, wherein the substituent if present is a branched or unbranched $C_1$–$C_6$ alkyl group or branched or unbranched $C_2$–$C_6$ alkenyl or alkynyl group;

wherein R3 is H, branched or unbranched $C_1$–$C_6$ alkyl, branched or unbranched $C_2$–$C_6$ alkenyl or alkynyl, $C_3$–$C_7$ cycloalkyl, $C_3$–$C_7$ cycloalkylalkyl, aryl, heteroaryl, aryl-($C_1$–$C_6$)-alkyl, heteroaryl-($C_1$–$C_6$)-alkyl, substituted $C_1$–$C_6$ alkyl, substituted $C_3$–$C_7$ cycloalkyl, substituted aryl, substituted heteroaryl, substituted aryl-($C_1$–$C_6$)-alkyl, or substituted heteroaryl-($C_1$–$C_6$)-alkyl, wherein the substituent if present is a halogen, CN, nitro, $C_1$–$C_6$ alkyl, OR14, SR14, N(R14)$_2$, SO$_2$N(R14)$_2$, CO$_2$R14, SO$_3$R14, N(R14)COR14, CON(R14)$_2$, or N(R14)CON(R14)$_2$;

wherein R4 is H or $CH_3$;

wherein R5 is H, branched or unbranched $C_1$–$C_6$ alkyl, branched or unbranched $C_2$–$C_6$ alkenyl or alkynyl, $C_3$–$C_7$ cycloalkyl, $C_3$–$C_7$ cycloalkylalkyl, aryl, heteroaryl, aryl-($C_1$–$C_6$)-alkyl, heteroaryl-($C_1$–$C_6$)-alkyl, substituted $C_1$–$C_6$ alkyl, substituted $C_3$–$C_7$ cycloalkyl, substituted aryl, substituted heteroaryl, substituted aryl-($C_1$–$C_6$)-alkyl, or substituted heteroaryl-($C_1$–$C_6$)-alkyl, wherein the substituent if present is a halogen, CN, nitro, $C_1$–$C_6$ alkyl, OR14, SR14, N(R14)$_2$, SO$_2$N(R14)$_2$, CO$_2$R14, SO$_3$R14, N(R14)COR14, CON(R14)$_2$, or N(R14)CON(R14)$_2$;

wherein R6 is H, branched or unbranched $C_1$–$C_6$ alkyl, branched or unbranched $C_2$–$C_6$ alkenyl or alkynyl, $C_3$–$C_7$ cycloalkyl, $C_3$–$C_7$ cycloalkylalkyl, aryl, heteroaryl, aryl-($C_1$–$C_6$)-alkyl, heteroaryl-($C_1$–$C_6$)-alkyl, substituted $C_1$–$C_6$ alkyl, substituted $C_3$–$C_7$ cycloalkyl, substituted aryl, substituted heteroaryl, substituted aryl-($C_1$–$C_6$)-alkyl, or substituted heteroaryl-($C_1$–$C_6$)-alkyl, wherein the substituent if present is a halogen, CN, nitro, $C_1$–$C_6$ alkyl, OR14, SR14, N(R14)$_2$, SO$_2$N(R14)$_2$, CO$_2$R14, SO$_3$R14, N(R14)COR14, CON(R14)$_2$, or N(R14)CON(R14)$_2$; and wherein R14 is independently H or branched or unbranched $C_1$–$C_6$ alkyl.

The invention is additionally directed towards a method of treating a subject afflicted with a disease which is susceptible to treatment by antagonism of the human $\alpha_{1d}$ adrenergic receptor which comprises administering to the subject an amount of the compound of the invention effective to treat the disease.

The treatment of the disease includes the reduction, remission, or regression of the disease or reduction of or relief from symptoms of the disease.

This invention is directed towards a method of treating a subject afflicted with hypertension which comprises administering to the subject an amount of the compound of this invention effective to treat hypertension.

This invention is directed towards a method of treating a subject afflicted with Raynaud's disease which comprises administering to the subject an amount of the compound of this invention effective to treat Raynaud's disease.

In one embodiment, the compound additionally does not cause hypotension at dosages effective to treat Raynaud's disease.

This invention is directed towards a method of treating a subject afflicted with urinary incontinence which comprises administering to the subject an amount of the compound of this invention effective to treat urinary incontinence.

In one embodiment, the compound additionally does not cause hypotension at dosages effective to treat urinary incontinence.

This invention is directed towards a method of treating urinary incontinence in a subject which comprises administering to the subject a therapeutically effective amount of a $\alpha_{1d}$ antagonist which binds to the human $\alpha_{1d}$ adrenergic receptor with a binding affinity which is at least ten-fold higher than the binding affinity with which the $\alpha_{1d}$ antagonist binds to (i) a human $\alpha_{1a}$ adrenergic receptor and (ii) a human $\alpha_{1b}$ adrenergic receptor, and the $\alpha_{1d}$ antagonist binds to the human $\alpha_{1d}$ adrenergic receptor with a binding affinity which is greater than the binding affinity with which the $\alpha_{1d}$ antagonist binds to a human 5-$HT_{1a}$ receptor.

In one embodiment, the $\alpha_{1d}$ antagonist binds to the human $\alpha_{1d}$ adrenergic receptor with a binding affinity which is at least 25-fold higher than the binding affinity with which the $\alpha_{1d}$ antagonist binds to (i) the human $\alpha_{1a}$ adrenergic receptor and (ii) the human $\alpha_{1b}$ adrenergic receptor, and the $\alpha_{1d}$ antagonist binds to the human $\alpha_{1d}$ adrenergic receptor with a binding affinity which is at least ten-fold higher than the binding affinity with which the $\alpha_{1d}$ antagonist binds to the human 5-$HT_{1a}$ receptor.

In one embodiment, the $\alpha_{1d}$ antagonist binds to the human $\alpha_{1d}$ adrenergic receptor with a binding affinity which is at least 25-fold higher than the binding affinity with which the $\alpha_{1d}$ antagonist binds to (i) the human $\alpha_{1a}$ adrenergic receptor, (ii) the human $\alpha_{1b}$ adrenergic receptor, and (iii) the human 5-$HT_{1a}$ receptor.

In another embodiment, the $\alpha_{1d}$ antagonist binds to the human $\alpha_{1d}$ adrenergic receptor with a binding affinity which is at least 100-fold higher than the binding affinity with which the $\alpha_{1d}$ antagonist binds to (i) the human $\alpha_{1a}$ adrenergic receptor, (ii) the human $\alpha_{1b}$ adrenergic receptor, and (iii) the human 5-$HT_{1a}$ receptor.

In another embodiment, the $\alpha_{1d}$ antagonist additionally does not cause hypotension at dosages effective to treat urinary incontinence.

One skilled in the art will readily appreciate that appropriate biological assays will be used to determine the therapeutic potential of the claimed compounds for treating the above noted disorders.

In connection with this invention, a number of cloned human receptors discussed herein, either as plasmids or as stable transfected cell lines, have been made pursuant to, and in satisfaction of, the Budapest Treaty on the International Recognition of the Deposit of Microorganisms for the Purpose of Patent Procedure, and are deposited with the American Type Culture Collection, 12301 Parklawn Drive, Rockville, Md. 20852. Specifically, these deposits have been accorded ATCC Accession Numbers as follows in Table 1.

TABLE 1

ATCC Deposits

| Designation | Cloned Receptor | ATCC Accession No. | Date of Deposit |
|---|---|---|---|
| Cell line L-$\alpha_{1A}$ | human $\alpha_{1d}$ (old human $\alpha_{1a}$) | CRL 11138 | Sept. 25, 1992 |
| Cell line L-$\alpha_{1B}$ | human $\alpha_{1b}$ | CRL 11139 | Sept. 25, 1992 |
| Cell line L-$\alpha_{1C}$ | human $\alpha_{1a}$ (old human $\alpha_{1c}$) | CRL 11140 | Sept. 25, 1992 |
| Cell line 5HT1A-3 | human 5-$HT_{1a}$ | CRL 11889 | May 11, 1995 |
| Cell line | human 5-$HT_{1D\alpha}$ | CRL 10421 | Apr. 17, 1990 |

TABLE 1-continued

ATCC Deposits

| Designation | Cloned Receptor | ATCC Accession No. | Date of Deposit |
| --- | --- | --- | --- |
| Ltk-8-30-84 Cell line Ltk-11 | (human 5-HT$_{1D}$) human 5-HT$_{1D\beta}$ (human 5-HT$_{1B}$) | CRL 10422 | Apr. 17, 1990 |

Cell Transfections

Transient transfections of COS-7 cells with various plasmids were performed using the DEAE-Dextran method which is well-known to those skilled in the art. A plasmid comprising an expression vector for the receptor of interest was added to monolayers of COS-7 cells bathed in a DEAE-Dextran solution. In order to enhance the efficiency of transfection, dimethyl sulfoxide was typically also added, according to the method of Lopata (Lopata, et al., 1984). Cells were then grown under controlled conditions and used in experiments after about 72 hours.

Stable cell lines were obtained using means which are well-known in the art. For example, a suitable host cell was typically cotransfected, using the calcium phosphate technique, with a plasmid comprising an expression vector for the receptor of interest and a plasmid comprising a gene which allows selection of successfully transfected cells. Cells were then grown in a controlled environment, and selected for expression of the receptor of interest. By continuing to grow and select cells, stable cell lines were obtained expressing the receptors described and used herein.

Binding Assays

The binding of a test compound to a receptor of interest was generally evaluated by competitve binding assays using membrane preparations derived from cells which expressed the receptor. First, conditions were determined which allowed measurement of the specific binding of a compound known to bind to the receptor. Then, the binding of the known compound to the receptor in membrane preparations was evaluated in the presence of several different concentrations of the test compound. Binding of the test compound to the receptor resulted in a reduction in the amount of the known compound which was bound to the receptor. A test compound having a high affinity for the receptor of interest would displace a given fraction of the bound known compound at a concentration lower than the concentration which would be required if the test compound had a lower affinity for the receptor of interest.

This invention will be better understood from the Experimental Details which follow. However, one skilled in the art will readily appreciate that the specific methods and results discussed are merely illustrative of the invention as described more fully in the claims which follow thereafter.

Experimental Details

Synthesis

The compounds of Examples 6–20 may be obtained using the methods depicted in Schemes 1–5. In the Schemes, m is an integer from 0 to 2; n is an integer from 0 to 2; R1 and R2 (i) are independently H, branched or unbranched $C_1$–$C_6$ alkyl or alkoxy, branched or unbranched $C_2$–$C_6$ alkenyl or alkynyl, branched or unbranched $C_1$–$C_6$ hydroxyalkyl, hydroxy, substituted or unsubstituted aryl or aryl-($C_1$–$C_6$)-alkyl, or substituted or unsubstituted heteroaryl or heteroaryl-($C_1$–$C_6$)-alkyl, wherein the substituent if present is a halogen, CN, nitro, hydroxy, branched or unbranched $C_1$–$C_6$ alkyl or alkoxy group, or branched or unbranched $C_2$–$C_6$ alkenyl or alkynyl group; or (ii) taken together form a substituted or unsubstituted cycloalkyl ring containing 3–10 carbons, wherein the substituent if present is a branched or unbranched $C_1$–$C_6$ alkyl group or branched or unbranched $C_2$–$C_6$ alkenyl or alkynyl group; R3 is H, branched or unbranched $C_1$–$C_6$ alkyl, branched or unbranched $C_2$–$C_6$ alkenyl or alkynyl, $C_3$–$C_7$ cycloalkyl, $C_3$–$C_7$ cycloalkylalkyl, aryl, heteroaryl, aryl-($C_1$–$C_6$)-alkyl, heteroaryl-($C_1$–$C_6$)-alkyl, substituted $C_1$–$C_6$ alkyl, substituted $C_3$–$C_7$ cycloalkyl, substituted aryl, substituted heteroaryl, substituted aryl-($C_1$–$C_6$)-alkyl, or substituted heteroaryl-($C_1$–$C_6$)-alkyl, wherein the substituent if present is a halogen, CN, nitro, $C_1$–$C_6$ alkyl, OR14, SR14, N(R14)$_2$, SO$_2$N(R14)$_2$, CO$_2$R14, SO$_3$R14, N(R14)COR14, CON (R14)$_2$, or N(R14)CON(R14)$_2$; R4 is H or CH$_3$; R5 is H, branched or unbranched $C_1$–$C_6$ alkyl, branched or unbranched $C_2$–$C_6$ alkenyl or alkynyl, $C_3$–$C_7$ cycloalkyl, $C_3$–$C_7$ cycloalkylalkyl, aryl, heteroaryl, aryl-($C_1$–$C_6$)-alkyl, heteroaryl-($C_1$–$C_6$)-alkyl, substituted $C_1$–$C_6$ alkyl, substituted $C_3$–$C_7$ cycloalkyl, substituted aryl, substituted heteroaryl, substituted aryl-($C_1$–$C_6$)-alkyl, or substituted heteroaryl-($C_1$–$C_6$)-alkyl, wherein the substituent if present is a halogen, CN, nitro, $C_1$–$C_6$ alkyl, OR14, SR14, N(R14)$_2$, SO$_2$N(R14)$_2$, CO$_2$R14, SO$_3$R14, N(R14)COR14, CON (R14)$_2$, or N(R14)CON(R14)$_2$; R6 is H, branched or unbranched $C_1$–$C_6$ alkyl, branched or unbranched $C_2$–$C_6$ alkenyl or alkynyl, $C_3$–$C_7$ cycloalkyl, $C_3$–$C_7$ cycloalkylalkyl, aryl, heteroaryl, aryl-($C_1$–$C_6$)-alkyl, heteroaryl-($C_1$–$C_6$)-alkyl, substituted $C_1$–$C_6$ alkyl, substituted $C_3$–$C_7$ cycloalkyl, substituted aryl, substituted heteroaryl, substituted aryl-($C_1$–$C_6$)-alkyl, or substituted heteroaryl-($C_1$–$C_6$)-alkyl, wherein the substituent if present is a halogen, CN, nitro, $C_1$–$C_6$ alkyl, OR14, SR14, N(R14)$_2$, SO$_2$N(R14)$_2$, CO$_2$R14, SO$_3$R14, N(R14)COR14, CON (R14)$_2$, or N(R14)CON(R14)$_2$; R7 is H, branched or unbranched $C_1$–$C_6$ alkyl, branched or unbranched $C_2$–$C_6$ alkenyl or alkynyl, $C_3$–$C_7$ cycloalkyl, aryl, aryl-($C_1$–$C_6$)-alkyl, CO$_2$R14, CON(R14)$_2$, substituted $C_1$–$C_6$ alkyl, substituted aryl, wherein the substituent is N(R14)$_2$, halogen, OR14 or SR14; R8 is H or CH$_3$; R9 is H, F, Cl, Br, branched or unbranched $C_1$–$C_6$ alkyl or alkoxy, CN; R10 is H or F; R11 is H, F, Cl, Br, I, CN, branched or unbranched $C_1$–$C_6$ alkyl or alkoxy; R12 is H, F, Cl, CN, branched or unbranched $C_1$–$C_6$ alkyl or alkoxy; R13 is H or F; X is N or CH; with the proviso that when R11 and R12 are each H, then R9 is F; and R14 is independently H or branched or unbranched $C_1$–$C_6$ alkyl.

When the substituents contain (an) amino, amido, carboxylic acid, and/or hydroxyl group(s), it may be necessary to incorporate protection and deprotection strategies into schemes 1 and 2. Methods for protection/deprotection of such groups are well-known in the art, and may be found, for example, in Greene, et al., 1991.

The following examples are merely illustrative of the methods used to synthesize compounds claimed in this patent. Examples 1–5 describe methods for making compounds that are precursors of the compounds of this invention.

Example 1

8-(2-Chloroethyl)-8-azaspiro[4.5]decane-7,9-dione

Compound 1

The synthesis of the compound of example 1 has been described previously by others (Wu, Y. H., 1968) and the procedure was modified as follows. A mixture of 3,3-tetramethyleneglutaric anhydride (10.01 g, 59.5 mmol) and ethanolamine (7.28 g, 119 mmol) in pyridine (120 mL) was heated at reflux for 3 hours. The solvent was removed and the residue was partitioned between 1 N HCl (50 mL) and ethyl acetate (50 mL). The aqueous layer was extracted with ethyl acetate (2×50 mL). The combined ethyl acetate fractions were dried over sodium sulfate and then the solvent was removed, leaving a clear oil (11.58 g). The oil in benzene (140 mL) and pyridine (7.7 mL) was cooled to 0° C. Thionyl chloride (7.0 mL) was slowly added to the mixture and then the solution was heated at 60° C. for 60 minutes. The solution was cooled to room temperature and water (100 mL) was added. The layers were separated and the aqueous layer was extracted with ethyl acetate (100 mL). The solvent was removed from the combined organic fractions and the residue was purified by flash chromatography over silica gel, eluting with hexane/ethyl acetate (3:1). The solvent was removed from fractions with $R_f$=0.3, giving the title compound as a pale yellow oil (6.19 g, 26.9 mmol, 45%). $^1$H NMR (300 MHz, CDCl$_3$) δ4.16 (t, 2H, J=6.5 Hz), 3.66 (t, 2H, J=6.3 Hz), 2.63 (s, 4H), 1.77–1.67 (m, 4H), 1.55–1.48 (m, 4H).

EXAMPLE 2

8-[(1R)-2-Chloro-1-methylethyl]-8-azaspiro[4.5]decane-7,9-dione

Compound 2

A mixture of 3,3-tetramethyleneglutaric anhydride (1.12 g, 6.66 mmol) and (R)-(−)-2-amino-1-propanol (1.00 g, 13.3 mmol) in pyridine (15 mL) was heated at reflux for 3 hours. The solvent was removed and the residue was partitioned between 1 N HCl (10 mL) and ethyl acetate (10 mL). The aqueous layer was extracted with ethyl acetate (2×10 mL). The combined ethyl acetate fractions were dried over sodium sulfate and then the solvent was removed, leaving a clear oil (1.92 g). A portion of this oil (0.70 g) in benzene (9 mL) and pyridine (0.40 mL) was cooled to 0° C. Thionyl chloride (0.40 mL) was slowly added to the mixture and then the solution was heated at 60° C. for 90 minutes. The solution was cooled to room temperature and water (10 mL) was added. The layers were separated and the aqueous layer was extracted with ethyl acetate (2×10 mL). The solvent was removed from the combined organic fractions and the residue was purified by flash chromatography over silica gel, eluting with hexane/ethyl acetate (3:1). The solvent was removed from fractions with $R_f$=0.3, giving the title compound as a pale yellow oil (294 mg, 1.21 mmol, 18%). $^1$H NMR (300 MHz, CDCl$_3$) δ5.09–5.04 (m, 1H), 4.17 (t, 1H, J=10.5 Hz), 3.66 (dd, 1H, J=11.1, 5.7 Hz), 2.61 (s, 4H), 1.76–1.69 (m, 4H), 1.56–1.51 (m, 4H), 1.40 (d, 3H, J=6.9 Hz).

EXAMPLE 3

(2,5-Difluorophenyl)piperazine

Compound 3

A mixture of 2,5-difluoroaniline (2.58 g, 20 mmol) and bis(2-chloroethyl)amine hydrochloride (3.96 g, 22 mmol) in butanol (10 mL) was heated at reflux for 24 hours. The mixture was cooled to room temperature, sodium carbonate (2.33 g, 22 mmol) was added, and the mixture was heated again at reflux. After 2 days, the mixture was cooled to room temperature, hexane (15 mL) and 3 N NaOH (25 mL) were added, and the resulting layers were separated. The aqueous layer was extracted with chloroform (3×25 mL) and the combined organic fractions were flashed over a column of silica gel. The silica gel was further eluted with a gradient of chloroform to chloroform/methanol (4:1). The solvent was removed from the combined fractions with $R_f$=0.14 [silica gel, chloroform/methanol (4:1)], giving the title compound as a yellow oil (0.606 g, 3.1 mmol, 15%). ESI-MS m/z 199 (MH$^+$).

EXAMPLE 4

(2,4,5-Trifluorophenyl)piperazine

Compound 4

A mixture of 2,4,5-trifluoroaniline (2.94 g, 20 mmol) and bis(2-chloroethyl)amine hydrochloride (3.56 g, 20 mmol) in butanol (10 mL) was heated at reflux for 24 hours. The mixture was cooled to room temperature, sodium carbonate (2.33 g, 22 mmol) was added, and the mixture was heated again at reflux. After 2 days, the mixture was cooled to room temperature, hexane (15 mL) and 3 N NaOH (25 mL) were added, and the resulting layers were separated. The aqueous layer was extracted with chloroform (3×25 mL) and the combined organic fractions were flashed over a column of silica gel. The silica gel was further eluted with a gradient of chloroform to chloroform/methanol (4:1). The solvent was removed from the combined fractions with $R_f$=0.20 [silica gel, chloroform/methanol (4:1)], giving the title compound as a yellow oil (1.028 g, 4.76 mmol, 24%). ESI-MS m/z 217 (MH$^+$).

EXAMPLE 5

4-(2,5-Dimethoxyphenyl)piperidine

Compound 5

A solution of tert-butyl lithium in pentane (1.7 M, 1.0 mL)was slowly added to a solution of 2-bromo-1,4-dimethoxybenzene (217 mg) in tetrahydrofuran (THF) (1.5 mL) at −78° C. The resulting solution was brought to room temperature and stirred for 30 minutes. Then the solution was cooled back down to −78° C. and a solution of 1-tert-butoxycarbonyl-4-piperidone (195 mg) was added. The resulting solution was stirred and allowed to warm to room temperature. After two hours, the reaction was quenched with aqueous NH$_4$Cl and the solvent was removed. The residue was purified by preparative TLC, giving the intermediate alcohol (222.3 mg, 66%). A portion of the alcohol (71.8 mg) was stirred at room temperature in trifluoroacetic acid (TFA) for two hours. The TFA was removed and the residue was purified by preparative TLC, giving the intermediate tetrahydropyridine (35.4 mg, 76%). A portion of the tetrahydropyridine (20.8 mg) in methanol (5 mL) was hydrogenated (balloon pressure) over 10% palladium on charcoal (5 mg) for 12 hours. The solution was filtered and the solvent was removed, giving the title compound as a white solid (21.0 mg, 100%, 50% overall). ESI-MS m/z 222 (MH$^+$).

EXAMPLE 6

8-{2-[4-(2,5-Difluorophenyl)piperazin-1-yl]ethyl}-8-azaspiro[4.5]decane-7,9-dione Compound 6

A mixture of 1-(2,5-difluorophenyl)piperazine (100 mg, 0.51 mmol) and 8-(2-chloroethyl)-8-azaspiro[4.5]decane-7,9-dione (100 mg, 0.44 mmol) was heated with stirring at 160° C. for 5 hours. The residue was dissolved in methanol, transferred to a preparative thin layer chromatographic plate (silica gel), and eluted with ethyl acetate/hexane (1:1). A band at $R_f$=0.7 was removed and rinsed with chloroform/methanol (4:1). The solvent was removed, giving the title compound as a pale yellow oil. $^1$H NMR (300 MHz, CDCl$_3$) δ6.99–6.89 (11-line m, 1H), 6.65–6.52 (m, 2H), 3.95 (t, 2H, J=6.5 Hz), 3.03 (t, 4H, J=4.7 Hz), 2.66 (t, 4H, J=4.7 Hz), 2.60 (s, 4H), 2.54 (t, 2H, J=6.6 Hz), 1.74–1.69 (m, 4H), 1.55–1.51 (m, 4H); ESI-MS m/z 392 (MH$^+$). The title compound was dissolved in ether and precipitated by addition of 1N HCl in ether, giving a white solid (64.9 mg, 0.15 mmol, 35%): mp 237–239° C., Anal. Calcd. for C$_{21}$H$_{27}$N$_3$F$_2$O$_2$·HCl: C, 58.94; H, 6.59; N, 9.82; F, 8.88. Found: C, 58.70; H, 6.46; N, 9.68; F, 9.00.

EXAMPLE 7
8-{2-[4-(2,4,5-Trifluorophenyl)piperazin-1-yl]ethyl}-8-azaspiro[4.5]decane-7,9-dione Compound 7

A mixture of 1-(2,4,5-trifluorophenyl)piperazine (0.94 g, 4.35 mmol) and 8-(2-chloroethyl)-8-azaspiro[4.5]decane-7,9-dione (1.00 g, 4.35 mmol) was heated with stirring at 160° C. for 7 hours. The residue was partitioned between ethyl acetate (40 mL) and saturated aqueous sodium carbonate (40 mL). The aqueous layer was extracted with ethyl acetate (2×40 mL) and the combined ethyl acetate fractions dried over sodium sulfate. The solvent was removed and the residue was purified by flash chromatography over silica gel, eluting with a gradient of hexane to hexane/ethyl acetate (1:1). The solvent was removed from the desired product [$R_f$=0.7, hexane/ethyl acetate (1:1)], leaving a pale tan oil which slowly solidified (0.652 g, 1.60 mmol, 37%, mp 230–234° C.). $^1$H NMR (300 MHz, CDCl$_3$) δ6.89 (ddd, 1H, J=11.7, 10.2, 7.5 Hz), 6.74 (dt, 1H, J=12.0, 8.1 Hz), 3.95 (t, 2H, J=6.6 Hz), 2.97 (t, 4H, J=4.7 Hz), 2.65 (t, 4H, J=4.7 Hz), 2.60 (s, 4H), 2.54 (t, 2H, J=6.5 Hz), 1.74–1.70 (m, 4H), 1.55–1.51 (m, 4H); $^{13}$C NMR (75 MHz, CDCl$_3$) δ172.7, 151.0 (ddd, J=243.8, 8.5, 1.7 Hz), 146.9 (ddd, J=241.6, 12.2, 3.2 Hz), 144.7 (ddd, J=242.3, 13.9, 12.4 Hz), 137.4 (ddd, J=9.6, 6.1, 2.9 Hz), 107.9 (dd, J=20.7, 4.1 Hz), 106.4 (dd, J=26.6, 21.5 Hz), 55.9, 53.6 (2C), 51.3 (d, 2C, J=3.0 Hz), 45.4 (2C), 40.1, 38.0 (2C), 36.9, 24.7 (2C); ESI-MS m/z 410 (MH$^+$). The title compound was dissolved in ether and precipitated by addition of 1N HCl in ether, giving a white solid. The solid was recrystallized from hot methanol/chloroform (4:1) (with hexane added to cloudiness), giving white flakes (0.43 g, 0.96 mmol, 22%): mp 234–236.5° C., Anal. Calcd. For C$_{21}$H$_{26}$N$_3$F$_3$O$_2$·1.2 HCl: C, 55.66; H, 6.05; N, 9.31; F, 12.58. Found: C, 56.06; H, 6.09; N, 9.21; F, 12.20.

EXAMPLE 8
8-{(1R)-2-[4-(2,5-Difluorophenyl)piperazin-1-yl]-1-methylethyl}-8-azaspiro[4.5]decane-7,9-dione Compound 8

A mixture of 1-(2,5-difluorophenyl)piperazine (20 mg, 0.10 mmol) and (R)-8-(2-chloro-1-methylethyl)-8-azaspiro[4.5]decane-7,9-dione (20 mg, 0.082 mmol) was heated with stirring at 160° C. for 5 hours. The residue was purified by preparative HPLC [reverse phase column (C$_{18}$ HC), water/methanol (70:30) with 0.1% TFA to water/methanol (40:60) with 0.1% TFA gradient, UV detection at λ254 nm or λ215 nm], giving (after removal of the solvent) the title compound as a pale yellow oil (21.5 mg, 0.05 mmol, 66%): ESI-MS m/z 406 (MH$^+$).

EXAMPLE 9
8-{(1R)-2-[4-(2,4,5-Trifluorophenyl)piperazin-1-yl]-1-methylethyl}-8-azaspiro[4.5]decane-7,9-dione Compound 9

A mixture of 1-(2,4,5-trifluorophenyl)piperazine (105 mg, 0.49 mmol) and (R)-8-(2-chloro-1-methylethyl)-8-azaspiro[4.5]decane-7,9-dione (105 mg, 0.43 mmol) was heated with stirring at 160° C. for 5 hours. The residue was dissolved in methanol, transferred to a preparative thin layer chromatographic plate (silica gel), and eluted with ethyl acetate/hexane (1:1). A band at Rf=0.8 was removed and rinsed with chloroform/methanol (4:1). The solvent was removed, giving the title compound as a pale yellow oil (86.2 mg, 0.20 mmol, 47%). $^1$H NMR (300 MHz, CDCl$_3$) δ6.89 (ddd, 1H, J=11.7, 10.2, 7.5 Hz), 6.71 (dt, 1H, J=12.0, 8.1 Hz), 5.08–4.96 (m, 1H), 3.14 (dd, 1H, J=12.6, 10.5 Hz), 2.92 (t, 4H, J=4.7 Hz), 2.73–2.66 (m, 2H), 2.58 (s, 4H), 2.51–2.44 (m, 2H), 2.36 (dd, 1H, J=12.6, 5.4 Hz), 1.75–1.68 (m, 4H), 1.57–1.50 (m, 4H), 1.34 (d, 3H, J=6.9 Hz); ESI-MS m/z 424 (MH$^+$). The title compound was dissolved in ether and precipitated by addition of 1N HCl in ether, giving a white solid: mp 231–235° C.

EXAMPLE 10
8-{(1S)-2-[4-(2,5-Difluorophenyl)piperazin-1-yl]-1-methylethyl}-8-azaspiro[4.5]decane-7,9-dione Compound 10

A mixture of 1-(2,5-difluorophenyl)piperazine (20 mg, 0.10 mmol) and (S)-8-(2-chloro-1-methylethyl)-8-azaspiro[4.5]decane-7,9-dione (20 mg, 0.082 mmol) was heated with stirring at 160° C. for 5 hours. The residue was purified by preparative HPLC (see Example 8 for conditions), giving (after removal of the solvent) the title compound as a pale yellow oil (10.8 mg, 0.026 mmol, 32%): ESI-MS m/z 406 (MH$^+$).

EXAMPLE 11
8-{(1S)-2-[4-(2,4,5-Trifluorophenyl)piperazin-1-yl]-1-methylethyl}-8-azaspiro[4.5]decane-7,9-dione Compound 11

A mixture of 1-(2,4,5-trifluorophenyl)piperazine (20 mg, 0.093 mmol) and (S)-8-(2-chloro-1-methylethyl)-8-azaspiro[4.5]decane-7,9-dione (20 mg, 0.082 mmol) was heated with stirring at 160° C. for 5 hours. The residue was purified by preparative HPLC (see Example 8 for conditions), giving (after removal of the solvent) the title compound as a pale yellow oil (18.1 mg, 0.043 mmol, 52%): ESI-MS m/z 424 (MH$^+$).

EXAMPLE 12
8-{2-[4-(5-Fluoro-2-methoxyphenyl)piperidin-1-yl]ethyl}-8-azaspiro[4.5]decane-7,9-dione Compound 12

A mixture of 4-(5-fluoro-2-methoxyphenyl)piperidine (20 mg, 0.096 mmol) and 8-(2-chloroethyl)-8-azaspiro[4.5]decane-7,9-dione(20 mg, 0.087 mmol) was heated with stirring at 165° C. for 1 hour. The residue was purified by preparative HPLC (see Example 8 for conditions), giving (after removal of the solvent) the title compound as a pale yellow oil (2.6 mg, 0.0065 mmol, 7%): ESI-MS m/z 403 (MH$^+$).

EXAMPLE 13
8-{2-[4-(5-Chloro-2-methylphenyl)piperazino]ethyl}-8-azaspiro [4.5]decane-7,9-dione Compound 13

A mixture of 1-(5-chloro-2-methylphenyl)piperazine (20 mg, 0.095 mmol) and 8-(2-chloroethyl)-8-azaspiro[4.5]decane-7,9-dione(20 mg, 0.087 mmol) was heated with stirring at 160° C. for 5 hours. The residue was purified by preparative HPLC (see Example 8 for conditions), giving (after removal of the solvent) the title compound as a pale yellow oil (17.3 mg, 0.043 mmol, 49%): ESI-MS m/z 404 (MH$^+$).

EXAMPLE 14
8-{2-[4-(2,6-Difluorophenyl)piperazino]ethyl}-8-azaspiro[4.5]decane-7,9-dione Compound 14

A mixture of 1-(2,6-difluorophenyl)piperazine (23.8 mg, 0.120 mmol) and 8-(2-chloroethyl)-8-azaspiro[4.5]decane-7,9-dione(20 mg, 0.087 mmol) was heated with stirring at 160° C. for 5 hours. The residue was purified by preparative HPLC (see Example 8 for conditions), giving (after removal of the solvent) the title compound as a pale yellow oil (8.9 mg, 0.023 mmol, 26%): ESI-MS m/z 392 (MH$^+$).

EXAMPLE 15
8-{2-[4-(3,4-Difluorophenyl)piperazin-1-yl]ethyl}-8-azaspiro[4.5]decane-7,9-dione
Compound 15

A mixture of 1-(3,4-difluorophenyl)piperazine (21.5 mg, 0.109 mmol) and 8-(2-chloroethyl)-8-azaspiro[4.5]decane-7,9-dione(20 mg, 0.087 mmol) was heated with stirring at 165° C. for 1 hour. The residue was purified by preparative HPLC (see Example 8 for conditions), giving (after removal of the solvent) the title compound as a pale yellow oil (13.7 mg, 0.035 mmol, 40%): ESI-MS m/z 392 (MH+).

EXAMPLE 16
8-{(1R)-1-Phenyl-2-[4-(2,4,5-trifluorophenyl)piperazino]ethyl}-8-azaspiro[4.5]decane-7,9-dione
Compound 16

A mixture of 1-(2,4,5-trifluorophenyl)piperazine (20 mg, 0.093 mmol) and (R)-8-(2-chloro-1-phenylethyl)-8-azaspiro[4.5]decane-7,9-dione (20 mg, 0.066 mmol) was heated with stirring at 160° C. for 5 hours. The residue was purified by preparative TLC, giving the title compound as an off-white solid (9.5 mg, 0.020 mmol, 30%): ESI-MS m/z 486 (MH+).

EXAMPLE 17
8-{(1R)-1-Benzyl-2-[4-(2,4,5-trifluorophenyl)piperazino]ethyl}-8-azaspiro[4.5]decane-7,9-dione
Compound 17

A mixture of 1-(2,4,5-trifluorophenyl)piperazine (20 mg, 0.093 mmol) 8-[(1R)-1-benzyl-2-chloroethyl]-8-azaspiro[4.5]decane-7,9-dione (20 mg, 0.063 mmol) was heated with stirring at 160° C. for 5 hours. The residue was purified by preparative TLC, giving the title compound as an off-white solid (4.7 mg, 0.0094 mmol, 15%): ESI-MS m/z 500 (MH+).

EXAMPLE 18

1-(2-Hydroxyethyl)-4-(2-fluorophenyl)piperazine
Compound 18

A mixture of 1-(2-fluorophenyl)piperazine (0.50 g), 2-iodoethanol (0.48 g), and potassium carbonate (1.5 g) in dimethylformamide (7 mL) was heated at reflux for three hours. The solvent was removed in vacuo and the residue was purified by preparative thin-layer chomatography (silica gel, eluting with chloroform/methanol, 9:1), giving the title compound as a yellow oil (0.41 g, 65%). $^1$H NMR (300 MHz, CDCl$_3$) δ7.09–6.90 (m, 4H), 3.67 (t, 2H, J=5.4 Hz), 3.13 (t, 4H, J=4.7 Hz), 2.76 (br s, 1H), 2.71 (t, 4H, J=4.8 Hz), 2.63 (t, 4H, J=5.4 Hz). $^{13}$C NMR (75 MHz, CDCl$_3$) δ156.3 (d, J=244.1 Hz), 140.6 (d, J=8.8 Hz), 125.1 (d, J=3.4 Hz), 123.2 (d, J=8.1 Hz), 119.5 (d, J=2.9 Hz), 116.7 (d, J=20.6 Hz), 60.1, 58.4, 53.6 (2C), 51.2 (d, 2C, J=3.0 Hz).

EXAMPLE 19
1-(2-Chloroethyl)-4-(2-fluorophenyl)piperazine
Compound 19

Thionyl chloride (1 mL) was added dropwise to an ice-cooled solution of 1-(2-hydroxyethyl)-4-(2-fluorophenyl)piperazine (300 mg) and pyridine (1 mL) in benzene (20 mL). After 30 minutes the solution was brought to room temperature and then the flask was immersed in a 60° C. oil bath for 1 hour. The layers were separated and the aqueous fraction was extracted with ethyl acetate (2×20 mL). The combined organic fractions were dried over sodium sulfate and the solvent was removed in vacuo, giving the desired product as a yellow solid (58.6 mg, 18%). ESI-MS m/z 243 (MH+).

EXAMPLE 20
8-{2-[4-(2-Fluorophenyl)piperazin-1-yl]ethyl}-8-azaspiro[4.5]decane-7,9-dione
Compound 20

A mixture of 3,3-tetramethylene glutarimide (6.9 mg) and potassium carbonate (40 mg) in dimethylformamide (0.5 mL) was stirred at room temperature for 30 minutes. 1-(2-Chloroethyl)-4-(2-fluorophenyl)piperazine (10.0 mg) was added and the resulting solution was heated at 120° C. for 3 hours. The solvent was removed and the residue was purified by thin-layer chomatography (silica gel, eluting with hexane/ethyl acetate, 1:1), giving the title compound as a white solid (6.2 mg, 40%). $^1$H NMR (300 MHz, CDCl$_{13}$) δ7.07–6.87 (m, 4H), 3.96 (t, 2H, J=6.6 Hz), 3.05 (t, 4H, J=4.8 Hz), 2.67 (t, 4H, J=4.7 Hz), 2.59 (s, 4H), 2.54 (t, 4H, J=6.6 Hz), 1.73–1.68 (m, 4H), 1.55–1.50 (m, 4H). ESI-MS m/z 374 (MH+).

Scheme 1: General synthesis of compounds

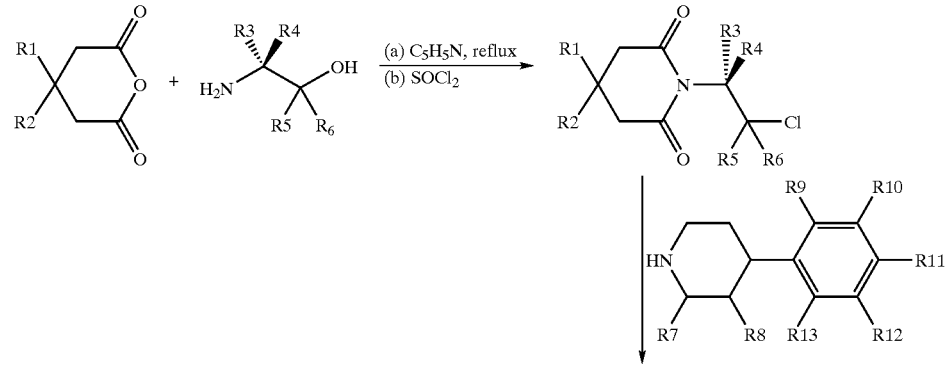

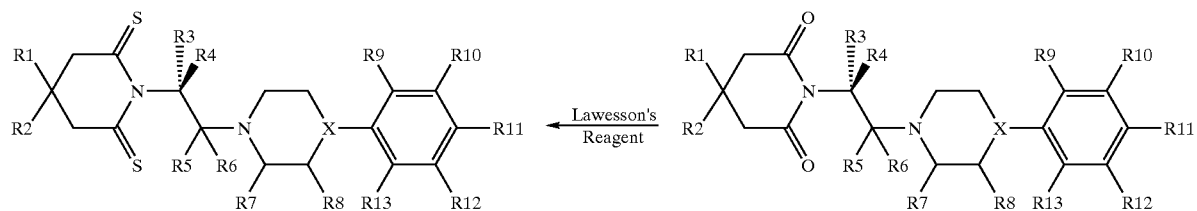
Scheme 2A: General synthesis of compounds
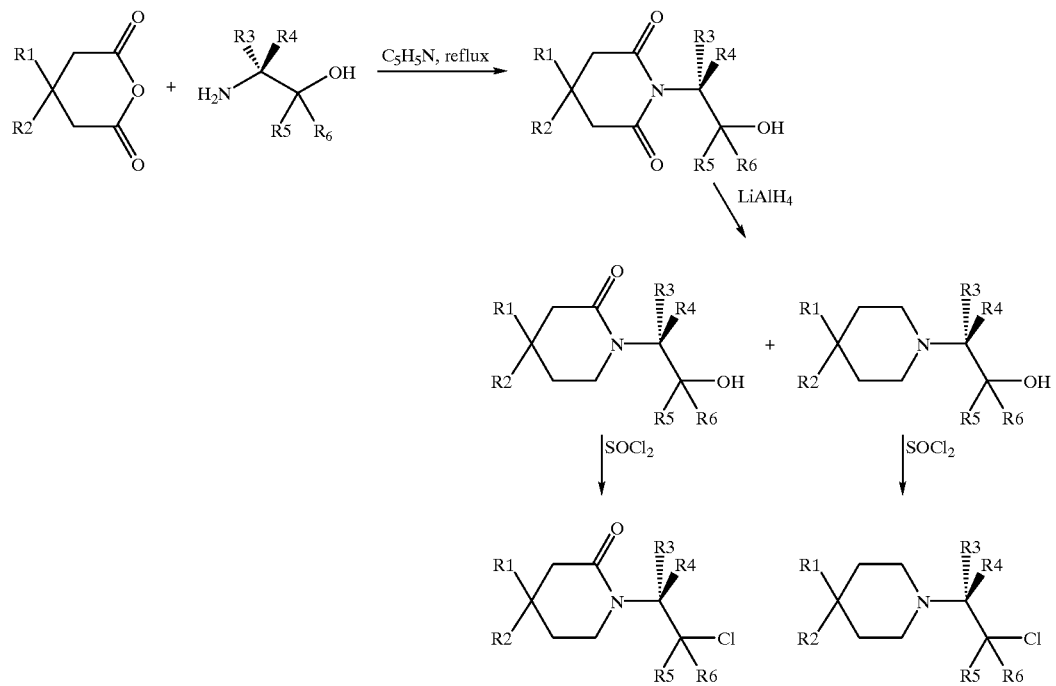
Scheme 2B: General synthesis of compounds
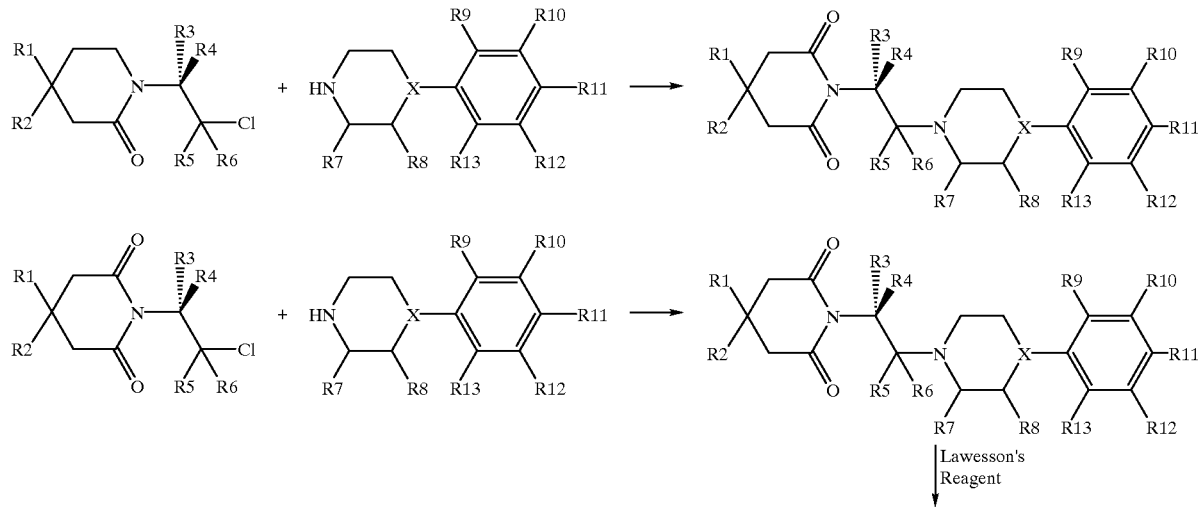

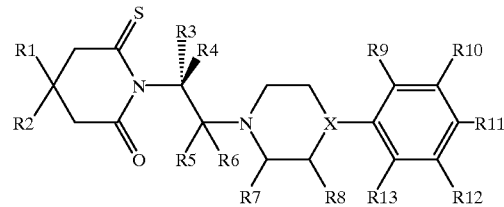
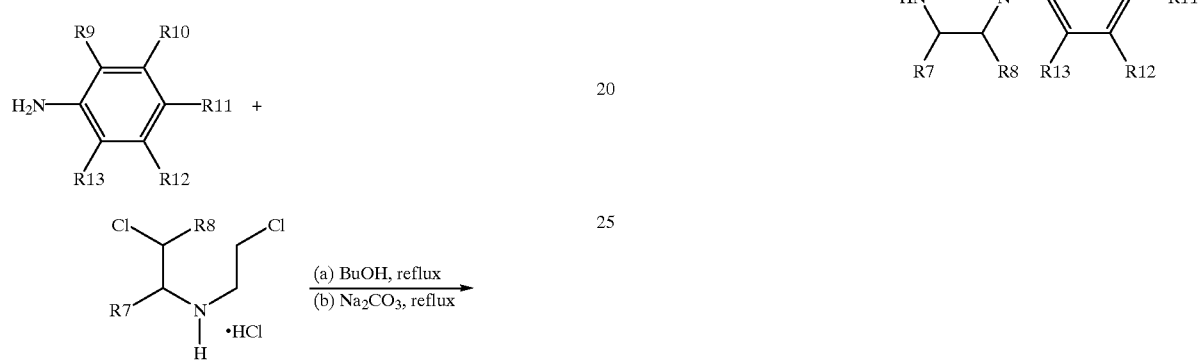
Scheme 3A: General thesis of piperazine precursors
Scheme 3B: General synthesis of piperazine precursors
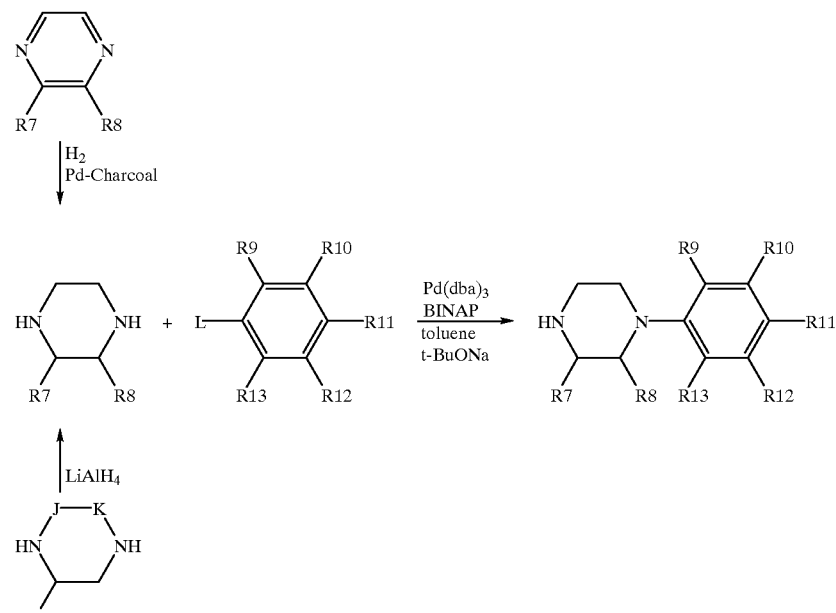
J = CH₂, C = O
K = CH₂, C = O
L = Br or I
M = CH₂, C = O, CHR8

Scheme 4: General synthesis of piperidine precursors

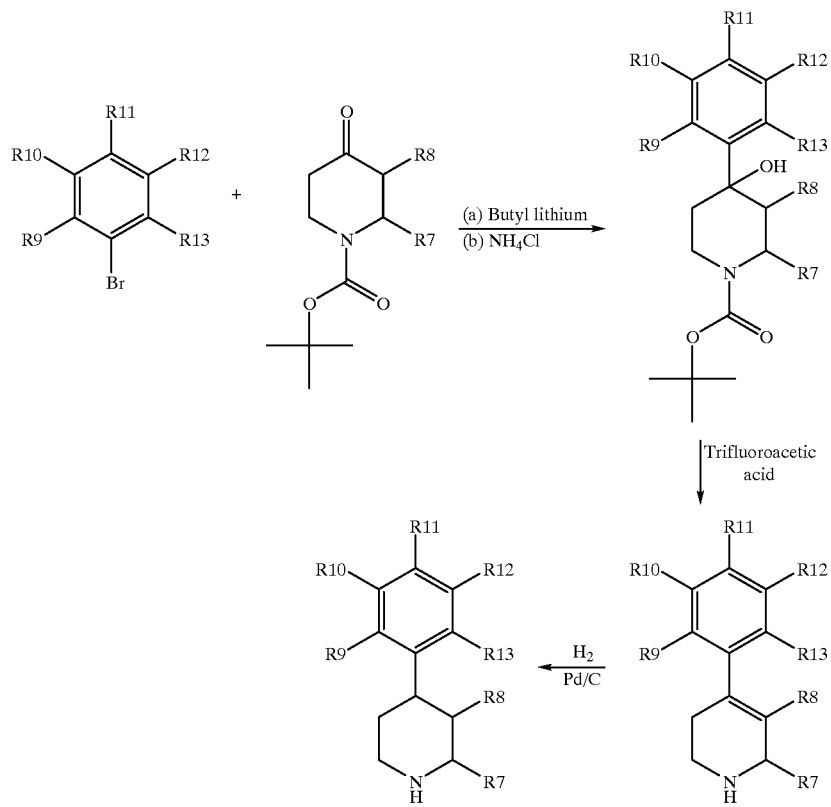

Scheme 5: General synthesis of compounds

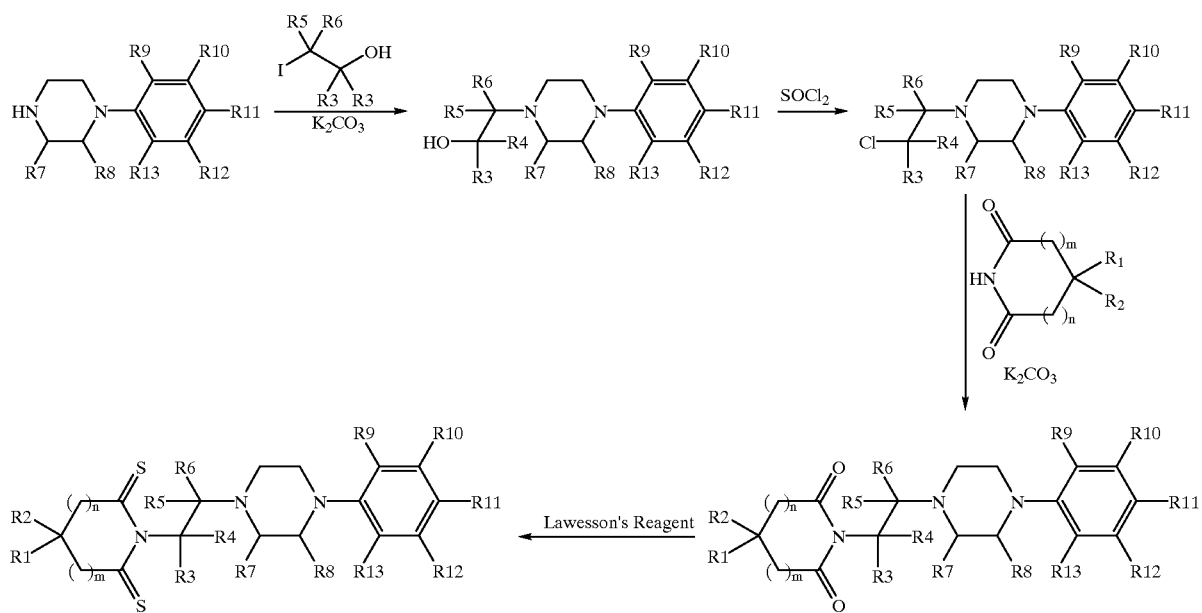

Oral Composition

As a specific embodiment of an oral composition of a compound of this invention, 100 mg of one of the compounds described herein is formulated with sufficient finely divided lactose to provide a total amount of 580 to 590 mg to fill a size O hard gel capsule.

Determination of the Binding Affinities of Compounds

Binding affinities were measured for selected compounds of the invention at three cloned human alpha-1 receptor subtypes, as well as at the 5-HT$_{1a}$ receptor.

The binding properties of compounds at the different human receptors were determined in vitro using cultured cell lines that selectively express the receptor of interest. These cell lines were prepared by transfecting the cloned cDNA or cloned genomic DNA or constructs containing both genomic DNA and cDNA encoding the human receptors as described below.

$\alpha_{1d}$ Human Adrenergic Receptor: The entire coding region. of $\alpha_{1d}$ (1719 bp), including 150 base pairs of 5' untranslated sequence (5' UT) and 300 bp of 3' untranslated sequence (3' UT), was cloned into the BamHI and ClaI sites of the polylinker-modified eukaryotic expression vector pCEXV-3, called EXJ.HR. The construct involved the ligation of partial overlapping human lymphocyte genomic and hippocampal cDNA clones: 5' sequence were contained on a 1.2 kb SmaI-XhoI genomic fragment (the vector-derived BamHI site was used for subcloning instead of the internal insert-derived SmaI site) and 3' sequences were contained on a 1.3 kb XhoI-ClaI cDNA fragment (the ClaI site was from the vector polylinker). Stable cell lines were obtained by cotransfection with the plasmid $\alpha$1A/EXJ (expression vector containing the $\alpha_{1a}$ receptor gene (old nomenclature)) and the plasmid pGCcos3neo (plasmid containing the aminoglycoside transferase gene) into LM(tk-) cells using the calcium phosphate technique. The cells were grown, in a controlled environment (37° C., 5% $CO_2$), as monolayers in Dulbecco's modified Eagle's Medium (GIBCO, Grand Island, N.Y.) containing 25 mM glucose and supplemented with 10% bovine calf serum, 100 units/ml penicillin g, and 100 $\mu$g/ml streptomycin sulfate. Stable clones were then selected for resistance to the antibiotic G-418 (1 mg/ml), and membranes were harvested and assayed for their ability to bind [$^3$H]prazosin as described below (see Radioligand Binding assays).

The cell line expressing the human $\alpha_{1d}$ receptor used herein was designated L-$\alpha_{1A}$ (old nomenclature) and was deposited with the American Type Culture Collection, 12301 Parklawn Drive, Rockville, Md. 20852, U.S.A. under the provisions of the Budapest Treaty for the International Recognition of the Deposit of Microorganisms for the Purposes of Patent Procedure. The cell line expressing the human $\alpha_{1d}$ receptor, was accorded ATCC Accession No. CRL 11138, and was deposited on Sep. 25, 1992.

$\alpha_{1b}$ Human Adrenergic Receptor: The entire coding region of $\alpha_{1b}$ (1563 bp), including 200 base pairs of 5' untranslated sequence (5' UT) and 600 bp of 3' untranslated sequence (3' UT), was cloned into the EcoRI site of pCEXV-3 eukaryotic expression vector. The construct involved ligating the full-length EcoRI brainstem cDNA fragment from λ ZapII into the expression vector. Stable cell lines were selected as described above. Membranes were harvested and assayed for their ability to bind [$^3$H]prazosin as described below (see Radioligand Binding assays). The cell line used herein was designated L-$\alpha_{1B}$ and was deposited with the American Type Culture Collection, 12301 Parklawn Drive, Rockville, Md. 20852, U.S.A. under the provisions of the Budapest Treaty for the International Recognition of the Deposit of Microorganisms for the Purposes of Patent Procedure. The cell line L-$\alpha_{1B}$ was accorded ATCC Accession No. CR 11139, on Sep. 29, 1992.

$\alpha_{1a}$ Human Adrenergic Receptor: The entire coding region of $\alpha_{1a}$ (1401 bp), including 400 base pairs of 5' untranslated sequence (5' UT) and 200 bp of 3' untranslated sequence (3' UT), was cloned into the KpnI site of the polylinker-modified pCEXV-3-derived eukaryotic expression vector, EXJ.RH. The construct involved ligating three partial overlapping fragments: a 5'0.6 kb HincII genomic clone, a central 1.8 EcoRI hippocampal cDNA clone, and a 3'0.6 Kb PstI genomic clone. The hippocampal cDNA fragment overlaps with the 5' and 3' genomic clones so that the HincII and PstI sites at the 5' and 3' ends of the cDNA clone, respectively, were utilized for ligation. This full-length clone was cloned into the KpnI site of the expression vector, using the 5' and 3' KpnI sites of the fragment, derived from vector (i.e., pBluescript) and 3'-untranslated sequences, respectively. Stable cell lines were selected as described above. Membranes were harvested and assayed for their ability to bind [$^3$H]prazosin as described below (see Radioligand Binding assays). The stable cell line expressing the human $\alpha_{1a}$ receptor used herein was designated L-$\alpha_{1C}$ (old nomenclature) and was deposited with the American Type Culture Collection, 12301 Parklawn Drive, Rockville, Md. 20852, U.S.A. under the provisions of the Budapest Treaty for the International Recognition of the Deposit of Microorganisms for the Purposes of Patent Procedure. The cell line expressing the human $\alpha_{1a}$ receptor was accorded Accession No. CR 11140, on Sep. 25, 1992.

Radioligand Binding Assays for $\alpha_1$ Human Adrenergic Receptors: Transfected cells from culture flasks were scraped into 5 ml of 5 mM Tris-HCl, 5 mM EDTA, pH 7.5, and lysed by sonication. The cell lysates were centrifuged at 1000 rpm for 5 min at 4° C., and the supernatant was centrifuged at 30,000×g for 20 min at 4° C. The pellet was suspended in 50 mM Tris-HCl, 1 mM $MgCl_2$, and 0.1% ascorbic acid at pH 7.5. Binding of the $\alpha_1$, antagonist [$^3$H]prazosin (0.5 nM, specific activity 76.2 Ci/mmol) to membrane preparations of LM(tk-) cells was done in a final volume of 0.25 ml and incubated at 37° C. for 1 hour. Nonspecific binding was determined in the presence of 10 $\mu$M phentolamine. The reaction was stopped by filtration through GF/B filters using a cell harvester. Inhibition experiments, routinely consisting of 6 concentrations of the tested compounds, were analyzed using a non-linear regression curve-fitting computer program to obtain Ki values.

5-HT$_{1a}$ receptor: The cell line for the 5-HT$_{1a}$ receptor, designated 5-HT1A-3, was deposited on May 11, 1995, and accorded ATCC Accession No. CRL 11889. The cDNA corresponding to the $^5$-HT$_{1a}$ receptor open reading frames and variable non-coding 5'- and 3'-regions, was cloned into the eukaryotic expression vector pCEXV-3. These constructs were transfected transiently into COS-7 cells by the DEAE-dextran method. Cells were harvested after 72 hours and lysed by sonication in 5 mM Tris-HCl, 5 mM EDTA, pH 7.5. The cell lysates were centrifuged at 1000 rpm for 5 minutes at 4° C., and the supernatant was centrifuged at 30,000×g for 20 minutes at 4° C. The pellet was suspended in 50 mM Tris-HCl buffer (pH 7.7 at room temperature) containing 10 mM $MgSO_4$, 0.5 mM EDTA, and 0.1% ascorbate. The affinity of compounds at 5-HT$_{1a}$ receptors were determined in equilibrium competition binding assays using [$^3$H]-8-OH-DPAT. Nonspecific binding was defined by the addition of 10 $\mu$M mianserin. The bound radioligand was separated by filtration through GF/B filters using a cell harvester.

5-HT$_{1D\alpha}$ (5-HT$_{1D}$) and 5-HT$_{1D\beta}$ (5-HT$_{1B}$) receptors: The cell lysates of the LM(tk-) clonal cell line stably transfected with the genes encoding each of these 5-HT receptor subtypes were prepared as described above. The cell line for the 5-HT$_{1D\alpha}$ (5-HT$_{1D}$) receptor, designated as Ltk-8-30-84, was deposited on Apr. 17, 1990, and accorded ATCC Accession No. CRL 10421. The cell line for the 5-HT$_{1D\beta}$ (5-HT$_{1B}$)

receptor, designated as Ltk-11, was deposited on Apr. 17, 1990, and accorded ATCC Accession No. CRL 10422. These preparations were suspended in 50 mM Tris-HCl buffer (pH 7.4 at 37° C.) containing 10 mM MgCl$_2$, 0.2 mM EDTA, 10 $\mu$M pargyline, and 0.1% ascorbate. The affinities of compounds were determined in equilibrium competition binding assays by incubation for 30 minutes at 37° C. in the presence of 5 nM [$^3$H] serotonin. Nonspecific binding was determined in the presence of 10 $\mu$M serotonin. The bound radioligand was separated by filtration through GF/B filters using a cell harvester.

The compounds described above were assayed using cloned human alpha adrenergic receptors and the cloned human serotonin receptors. The preferred compounds were found to be selective for the aid receptor. The binding affinities of several compounds are illustrated in the following table.

TABLE 2

Binding affinities (pKi) of selected compounds of the present invention at cloned human $\alpha_{1a}$, $\alpha_{1b}$, $\alpha_{1d}$, and 5-HT$_{1a}$ receptors

| Compound | $\alpha_{1a}$ | $\alpha_{1b}$ | $\alpha_{1d}$ | 5-HT$_{1a}$ |
|---|---|---|---|---|
| Compound 6 | 6.0 | 7.3 | 9.0 | 7.6 |
| Compound 7 | 5.4 | 6.4 | 8.7 | 6.4 |
| Compound 8 | 5.2 | 7.2 | 9.1 | 7.3 |
| Compound 9 | 4.8 | 6.8 | 8.9 | 6.5 |
| Compound 10 | 5.1 | 5.4 | 7.3 | 5.6 |
| Compound 11 | 4.9 | 5.3 | 6.9 | 5.5 |
| Compound 12 | 7.1 | 7.2 | 9.0 | 8.1 |
| Compound 13 | 5.1 | 5.5 | 7.4 | 6.6 |
| Compound 14 | 5.5 | 6.9 | 8.4 | 8.1 |
| Compound 15 | 5.4 | 5.8 | 8.1 | 7.3 |
| Compound 16 | 5.1 | 5.3 | 7.1 | |
| Compound 17 | 5.0 | 5.3 | 7.1 | |
| Compound 20 | 6.2 | 7.2 | 9.1 | 8.1 |

In addition, the binding affinities (pKi) of Compound 7 of the present invention at the cloned human 5-HT$_{1D\alpha}$ (5-HT$_{1D}$) and 5-HT$_{1D\beta}$(5-HT$_{1B}$) receptors are 6.1 and 5.3, respectively.

Functional Assays

The functional in vitro activity of Compound 7 was characterized in several pharmacologically defined $\alpha_1$ adrenoceptor subtype isolated tissue assays (Aboud et al., 1993). (Rat epididymal vas deferens was used to determine $\alpha_{1A}$ functional responses, spleen was used for $\alpha_{1B}$ responses, and thoracic aorta was used for $\alpha_{1D}$ responses.) Experiments were carried out according to the method of Deng et al., 1996, with minor buffer and tissue setup tension modifications. Krebs additionally contained 0.1 $\mu$M desipramine and 10 $\mu$M corticosterone to block neuronal and extra neuronal uptake, respectively, and 0.3 $\mu$M idazoxan to eliminate $\alpha_2$ mediated responses. Aorta and vas deferens strips were set at 0.5 g resting tension, and the splenic preparations were tensioned to 1 g. All preparations were equilibrated for 1 hr before the addition of drugs.

When added in concentrations up to 10 $\mu$M, Compound 7 failed to produce agonist activity at any of the three rat $\alpha_1$-AR subtype models. Additionally, its antagonist potency was determined by its ability to antagonize phenylephrine (PE) induced contraction in each of these preparations. The degree of shift of the PE agonist dose response-curve in the presence of Compound 7 was measured and pK$_B$ values were calculated (mean±s.e.m.). Compound 7 potently inhibited the effects of PE in the aorta (pK$_B$=8.5±0.2). It was approximately 2000 fold less potent in the vas deferens (pK$_B$=5.2±0.2) and approximately 60 fold less effective in the spleen (pK$_B$=6.7±0.2). This functional characterization indicates that Compound 7 is a highly selective, potent antagonist at the $\alpha_{1D}$ adrenergic receptor.

Contribution of $\alpha_{1D}$-adrenoceptors to Vascular Contractions in Electrically Stimulated vs Non-stimulated Arteries In order to assess whether $\alpha_{1A}$ and $\alpha_{1D}$-adrenoceptors are differentially innervated in resistance vessels, we compared antagonism by Compound 7 ($\alpha_{1D}$) and SNAP 6201 ($\alpha_{1A}$) (Schorn et al.,1999) in rat caudal arteries contracted by transmural stimulation of intrinsic neurons versus norepinephrine (NE) applied directly to the tissue bath.

Experimental Methods

Rings of rat caudal artery were positioned on L-shaped wire holders and suspended in Krebs' solution for measurement of isometric tension. Propranolol (3 $\mu$M), atropine (0.1 $\mu$M), and indomethacin (10 $\mu$M) were included in the buffer to prevent the activation of $\beta$-adrenoceptors and muscarinic receptors and prostaglandin formation. Tissue tension was adjusted to 0.5 g and thereafter readjusted twice. Control contractions were elicited by the application of NE (10 $\mu$M) or by electrical stimulation (trains of pulses: rate=0.01 trains/s; train duration=500 ms, frequency=9 Hz; pulse duration=4 ms; 90 volts). The effect of the $\alpha_{1D}$-selective Compound 7 and a selective $\alpha_{1A}$-adrenoceptor antagonist, each at a concentration 100-fold greater than its K$_B$ for that receptor, was evaluated in terms of: (1) its ability to reverse the contraction evoked by NE, and (2) its ability to inhibit the contraction evoked by electrical stimulation.

Results

Figure 2:
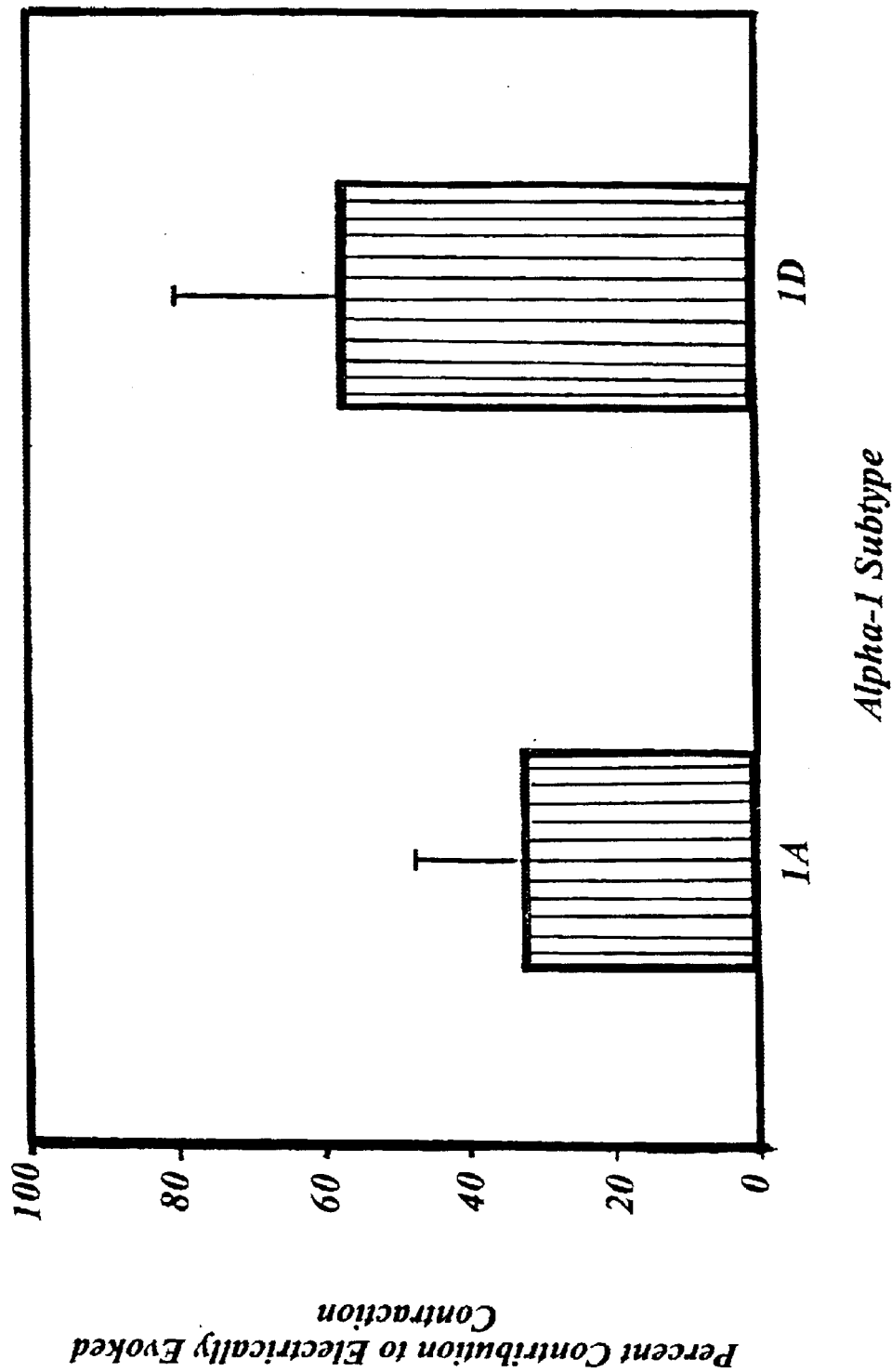
FIG. 2 Effects of $\alpha_{1D}$ and $\alpha_{1A}$ receptor blockade on contractions of the rat caudal artery evoked by electrical stimulation of intrinsic nerves.
Figure 3:
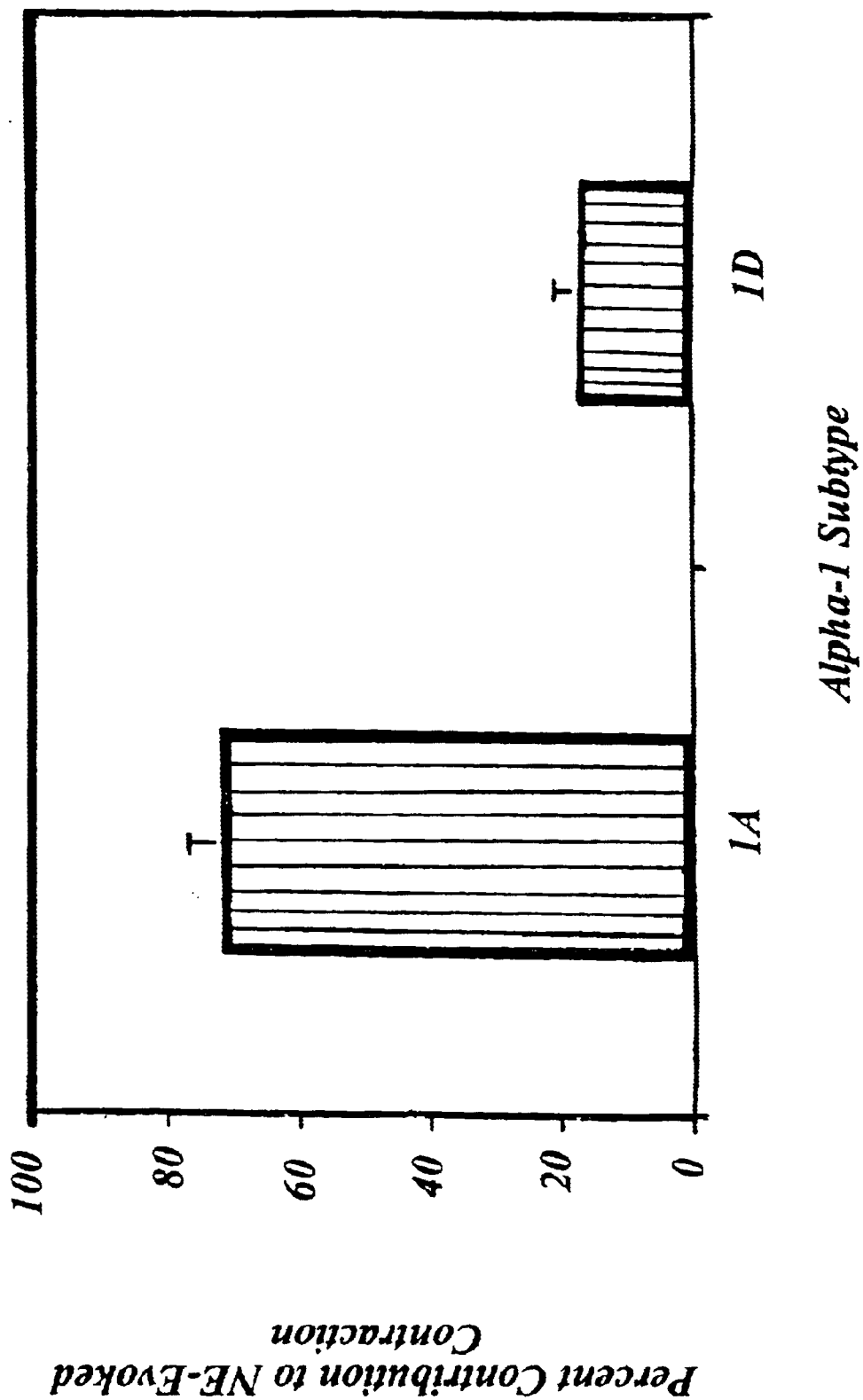
FIG. 3 Effects of $\alpha_{1D}$ and $\alpha_{1A}$ receptor blockade on contractions of the rat caudal artery evoked by application of norepinephrine to the tissue bath.

The results of these experiments indicate that the two methods give strikingly different indications of the role of the $\alpha_{1D}$ adrenoceptor in vascular contraction. When contractions are evoked by the application of NE to the tissue bath, a condition in which the agonist has equal access to synaptic as well as extrasynaptic receptors, $\alpha_{1D}$ receptor activation accounts for only 17% of the total contraction (FIG. 2). In contrast, when contractions are evoked by electrical stimulation of intrinsic nerves, a situation in which the actions of the released NE are restricted largely to receptors within the neuromuscular synapse, $\alpha_{1D}$ receptor activation accounts for the majority (58%) of the total contraction (FIG. 3). These results indicate that the $\alpha_{1D}$ adrenoceptor is the predominant subtype receiving innervation from sympathetic neurons in resistance arteries.

Effect of $\alpha_{1D}$-adrenoceptor Blockade in Anesthetized, Normotensive Rats The potential for $\alpha_{1D}$ selective antagonists as antihypertensive agents was reported by Deng et al (1996), based on studies with BMY 7378 in anesthetized, normotensive rats. BMY 7378 is an antagonist of the $\alpha_{1D}$ adrenoceptor which exhibits marked selectivity over other $\alpha$-adrenoceptors. However, BMY 7378 exhibits an even greater affinity at 5-HT$_{1A}$ receptors, at which it is a potent partial agonist. Furthermore, activation of central 5-HT$_{1A}$ receptors is known to result in a reduction in blood pressure. The possibility that the reduction of blood pressure seen with BMY 7378 in urethane-anesthetized rats was a result of 5-HT$_{1A}$ activation was not considered in the report by Deng et al. (1996). Therefore, we designed an experiment to test this possibility.

Experimental Methods

Rats were anesthetized with urethane and PE50 cannulae were placed in the femoral artery and vein for blood pressure monitoring and drug administration, respectively. After stabilization, rats were administered 200 $\mu$l saline vehicle or increasing doses of BMY 7378 or Compound 7 at 10 minutes intervals until the reduction in blood pressure reached a plateau. The 5-HT$_{1A}$-selective antagonist WAY 100635 (1 mg/kg) was then administered and blood pressure monitored for an additional 10 minutes.

Results

Figure 4:
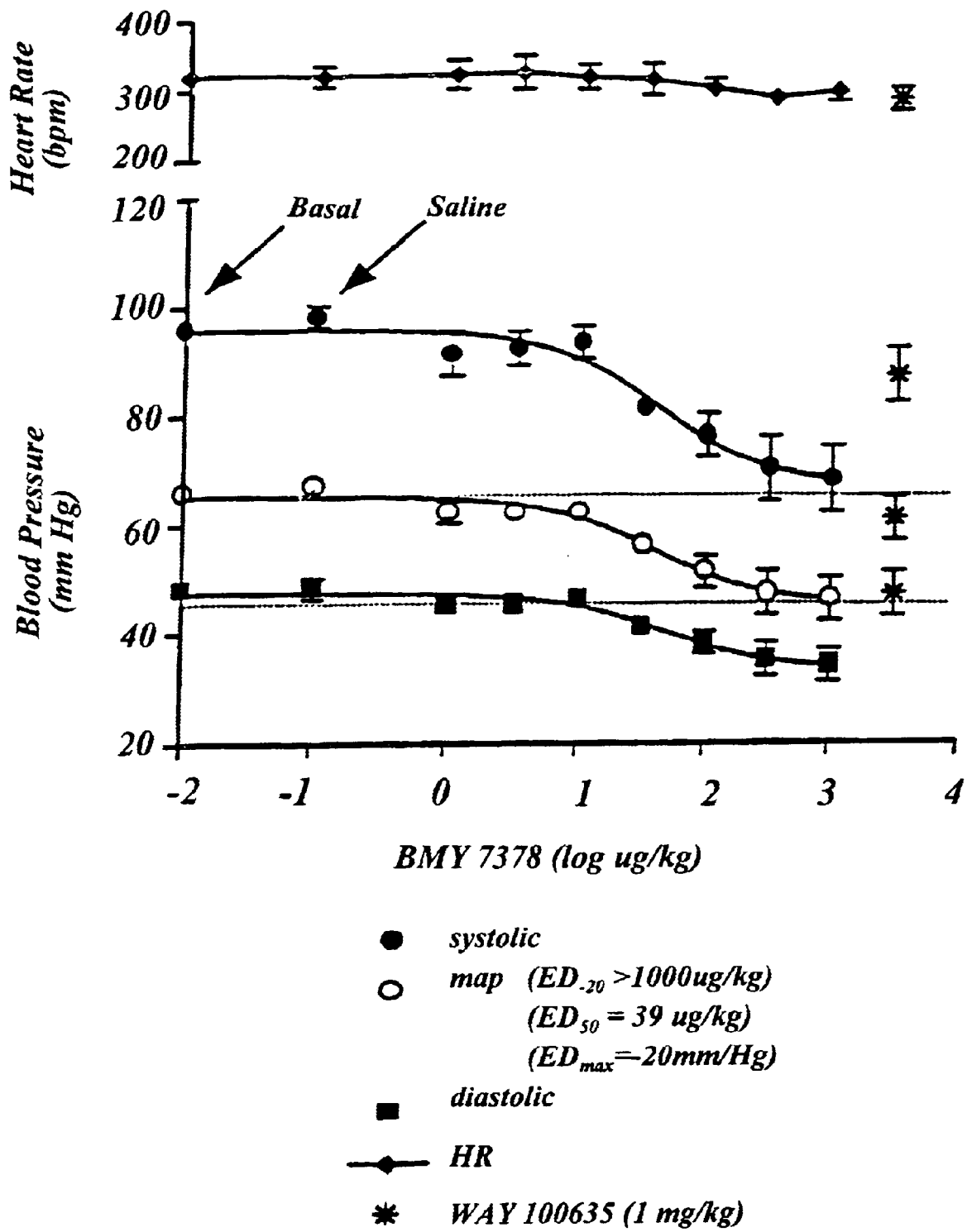
FIG. 4 Cardiovascular effects of BMY 7383 in urethane-anesthetized rats and effect (antagonism) of WAY 100635. n=4; 10 min post-dose.

FIG. 4 shows that BMY 7378 produces a dose-dependent reduction in systolic, diastolic and mean blood pressure which reaches a maximum effect at 300 to 1000 μg/kg. The effect of BMY 7378 on each of these parameters is reversed by the 5-HT$_{1A}$-selective antagonist WAY 100635, indicating that the effect is mediated predominately through activation of 5-HT$_{1A}$ receptors.

Figure 5:
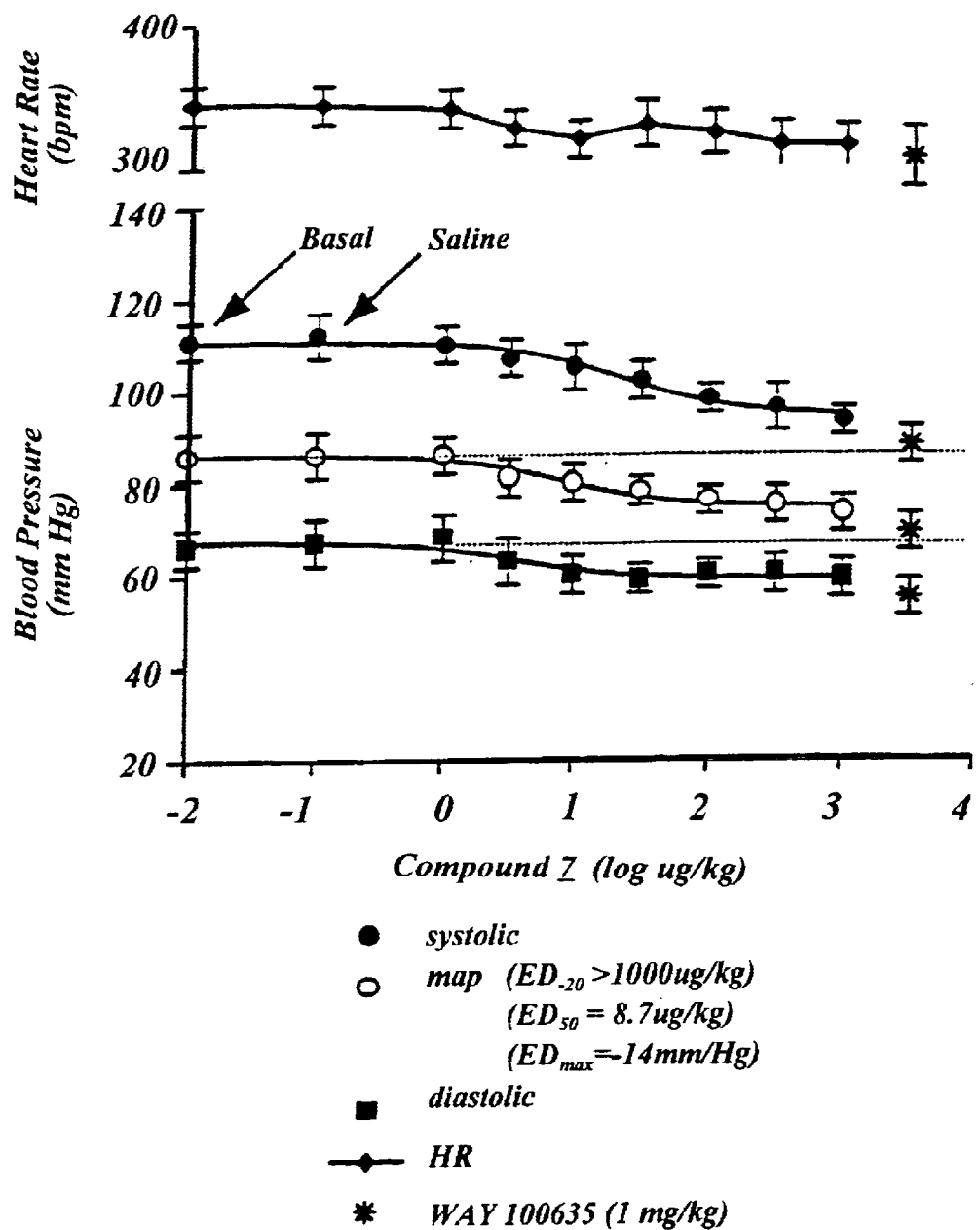
FIG. 5 Cardiovascular effects of Compound 7 in urethane-anesthetized rats and effect (antagonism) of WAY 100635. n=6; 10 min post-dose.

FIG. 5 shows that Compound 7 also reduces blood pressure in anesthetized rat, although to a lesser extent than BMY 7378. The effect is maximal at 100 to 300 μg/kg. In contrast to BMY 7378, however, this effect is not reversed by WAY 100635, indicating that it is solely a result of $\alpha_{1D}$ adrenoceptor blockade.

We conclude therefore that $\alpha_{1D}$ receptor blockade reduces blood pressure to a lesser extent than was previously thought, and that the effect is minor in anesthetized, normotensive rats. To further explore the potential cardiovascular liabilities of $\alpha_{1D}$ adrenoceptor blockade, we conducted experiments in conscious, normotensive rat.

Effect of $\alpha_{1D}$-adrenoceptor Blockade in Conscious, Normotensive Rats

Experimental Methods

Rats were anesthetized and a PE50 chronic indwelling cannula was placed in the abdominal aorta for measurement of blood pressure. On the following day, 5 rats each were administered vehicle (1% DMSO) or Compound 7 (4.0 mg/kg in 1% DMSO, i.v.) and mean blood pressure measurements were recorded at 0, 5, 30, and 60 minutes thereafter.

Results

Figure 6:
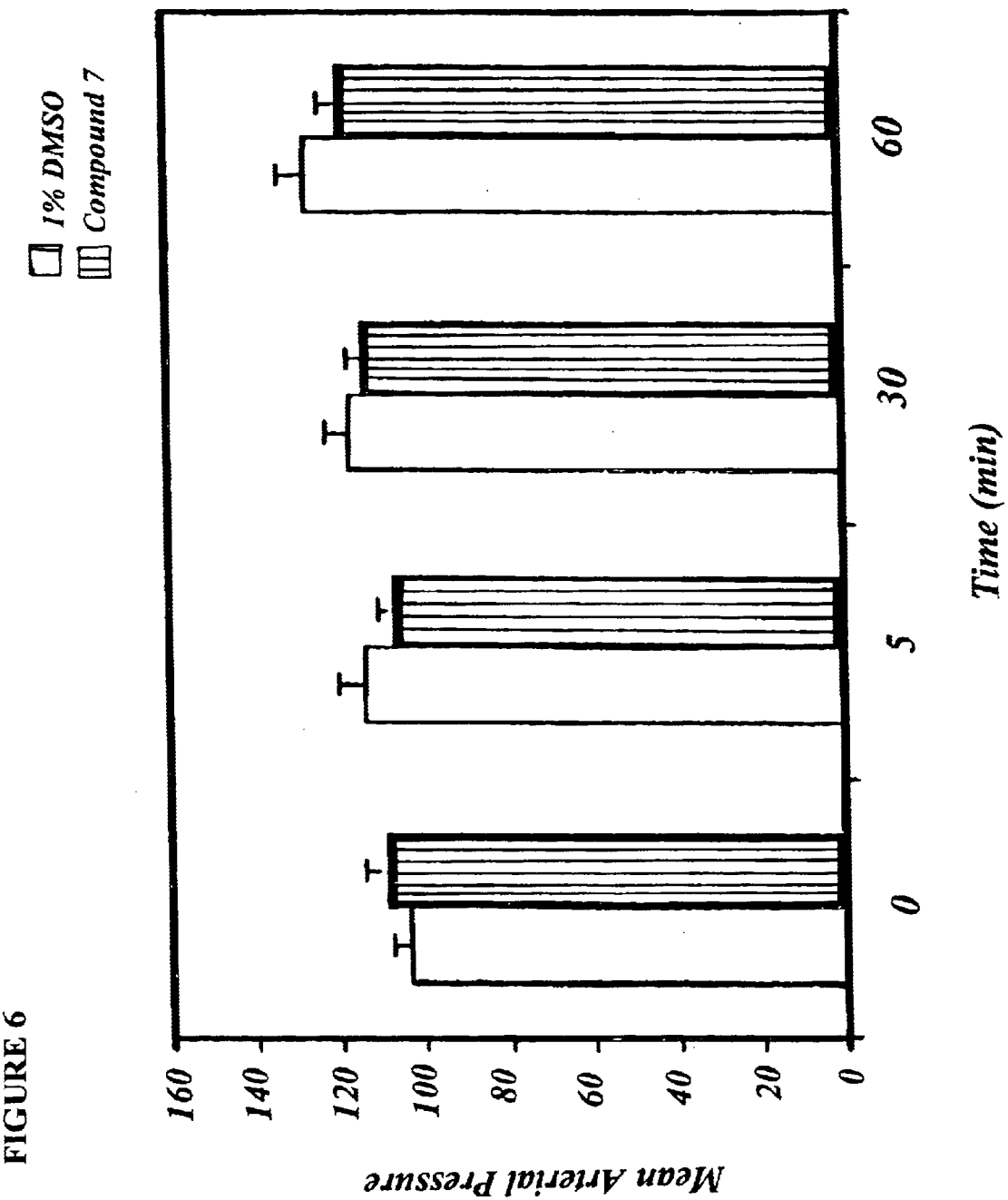
FIG. 6 Effect of the selective $\alpha_{1D}$ adrenoceptor antagonist Compound 7 on mean arterial blood pressure in conscious, normotensive rats.

No statistically significant changes in blood pressure were seen relative to vehicle-treated animals (FIG. 6).

Discussion of Cardiovascular Results $\alpha_{1D}$-adrenoceptor selective antagonists have been postulated to be of value in the treatment of hypertension. In one study (Deng et al., 1996) this conclusion was based on data obtained with the compound BMY 7378 in urethane-anesthetized, normotensive rats. The data presented herein demonstrate that their data were misinterpreted, i.e. BMY 7378 elicits its hypotensive effect predominately via activation of 5-HT$_{1A}$ receptors. The more selective $\alpha_{1D}$ antagonist, Compound 7 (see Table 2), elicits only a minor reduction in blood pressure in anesthetized animals and, more importantly, produces no reduction in blood pressure in conscious animals. Thus, we conclude that selective $\alpha_{1D}$ antagonists will be devoid of unwanted cardiovascular side effects in normotensive individuals.

In addition to the aforementioned studies in normotensive animals, an extensive study of $\alpha_1$-adrenoceptor subtype involvement has been made in spontaneously hypertensive rats (Scott et al., 1999). These studies employed 11 different antagonist with varying selectivity for $\alpha_1$-adrenoceptor subtypes. These authors concluded that the hypotensive potency of the antagonists in their study correlated best with their affinity for the $\alpha_{1D}$-adrenoceptor. The data presented in this application, obtained from experiments in normotensive rats, neither support nor contradict the results of the Scott et al., 1999 study.

REFERENCES

Aboud, R., et al. (1993) Br. J. Pharmacol. 109:80–87.
Broten, T., et al. (April, 1998) Experimental Biology Meeting, San Francisco, Calif., Abstract 2584.
Bylund, D. B. (1992) FASEB J. 6:832–9.
Deng, X. F. et al. (1996) Br. J. Pharmacol. 119:269–276.
Greene, T. W. and Wuts, P. G. M. (1991) Protective Groups in Organic Synthesis, 2nd Edition John Wiley & Sons, New York.
Hieble, et al. (1995) Pharmacological Reviews 47:267–270.
Lopata, et al. (1984) Nucl. Acids. Res. 12:5707–5717.
McGrath, et al. (1989) Med. Res. Rev., 9:407–533.
Schorn, T., et al. (1999) FASEB J., 13(4), Abstract 150.8.
Scott, A., et al. (1999) FASEB J., 13(4), Abstract 150.6.
Sokoloff, P. et al. (1990) Nature 146:347.
Wu, Y. H. U.S. Pat. No. 3,398,151, 1968.

What is claimed is:

1. A method of inhibiting activation of a human $\alpha_{1d}$ adrenergic receptor which comprises contacting the receptor with a compound so as to inhibit activation of the receptor, wherein the compound has the structure:

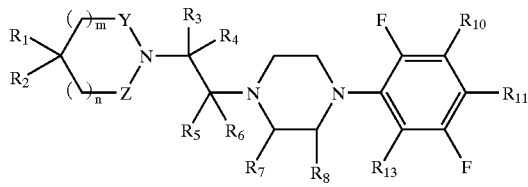

wherein each m and n is independently an integer from 0 to 2;
wherein each Y and Z is independently

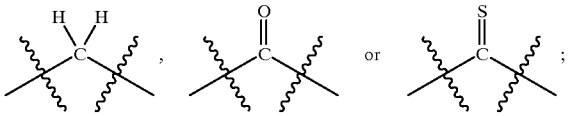

wherein $R_1$ and $R_2$ (i) are independently H, branched or unbranched $C_1$–$C_6$ alkyl or alkoxy, branched or unbranched $C_2$–$C_6$ alkenyl or alkynyl, branched or unbranched $C_1$–$C_6$ hydroxyalkyl, hydroxy, substituted or unsubstituted aryl or aryl-($C_1$–$C_6$)-alkyl, or substituted or unsubstituted heteroaryl or heteroaryl-($C_1$–$C_6$)-alkyl, wherein the substituent if present is a halogen, CN, nitro, hydroxy, branched or unbranched $C_1$–$C_6$ alkyl or alkoxy group, or branched or unbranched $C_2$–$C_6$ alkenyl or alkynyl group; or (ii) taken together form a substituted or unsubstituted cycloalkyl ring containing 3–10 carbons, wherein the substituent if present is a branched or unbranched $C_1$–$C_6$ alkyl group or branched or unbranched $C_2$–$C_6$ alkenyl or alkynyl group;

wherein $R_3$ is H, branched or unbranched $C_1$–$C_6$ alkyl, branched or unbranched $C_2$–$C_6$ alkenyl or alkynyl, $C_3$–$C_7$ cycloalkyl, $C_3$–$C_7$ cycloalkylalkyl, aryl, heteroaryl, aryl-($C_1$–$C_6$)-alkyl, heteroaryl-($C_1$–$C_6$)-alkyl, substituted $C_1$–$C_6$ alkyl, substituted $C_3$–$C_7$ cycloalkyl, substituted aryl, substituted heteroaryl, substituted aryl-($C_1$–$C_6$)-alkyl, or substituted heteroaryl-($C_1$–$C_6$)-alkyl, wherein the substituent if present is a halogen, CN, nitro, $C_1$–$C_6$ alkyl, $OR_{14}$, $SR_{14}$, $N(R_{14})_2$, $SO_2N(R_{14})_2$, $CO_2R_{14}$, $SO_3R_{14}$, $N(R_{14})COR_{14}$, CON $(R_{14})_2$, or $N(R_{14})CON(R_{14})_2$;

wherein $R_4$ is H or $CH_3$;

wherein $R_5$ is H, branched or unbranched $C_1$–$C_6$ alkyl, branched or unbranched $C_2$–$C_6$ alkenyl or alkynyl, $C_3$–$C_7$ cycloalkyl, $C_3$–$C_7$ cycloalkylalkyl, aryl, heteroaryl, aryl-($C_1$–$C_6$)-alkyl, heteroaryl-($C_1$–$C_6$)-alkyl, substituted $C_1$–$C_6$ alkyl, substituted $C_3$–$C_7$ cycloalkyl, substituted aryl, substituted heteroaryl, substituted aryl-($C_1$–$C_6$)-alkyl, or substituted heteroaryl-($C_1$–$C_6$)-alkyl, wherein the substituent if present is a halogen, CN, nitro, $C_1$–$C_6$ alkyl, $OR_{14}$, $SR_{14}$, $N(R_{14})_2$, $SO_2N(R_{14})_2$, $CO_2R_{14}$, $SO_3R_{14}$, $N(R_{14})COR_{14}$, $CON(R_{14})_2$, or $N(R_{14})CON(R_{14})_2$;

wherein $R_6$ is H, branched or unbranched $C_1$–$C_6$ alkyl, branched or unbranched $C_2$–$C_6$ alkenyl or alkynyl, $C_3$–$C_7$ cycloalkyl, $C_3$–$C_7$ cycloalkylalkyl, aryl, heteroaryl, aryl-($C_1$–$C_6$)-alkyl, heteroaryl-($C_1$–$C_6$)-alkyl, substituted $C_1$–$C_6$ alkyl, substituted $C_3$–$C_7$ cycloalkyl, substituted aryl, substituted heteroaryl, substituted aryl-($C_1$–$C_6$)-alkyl, or substituted heteroaryl-($C_1$–$C_6$)-alkyl, wherein the substituent if present is a halogen, CN, nitro, $C_1$–$C_6$ alkyl, $OR_{14}$, $SR_{14}$, $N(R_{14})_2$, $SO_2N(R_{14})_2$, $CO_2R_{14}$, $SO_3R_{14}$, $N(R_{14})COR_{14}$, $CON(R_{14})_2$, or $N(R_{14})CON(R_{14})_2$;

wherein $R_7$ is H, branched or unbranched $C_1$–$C_6$ alkyl, branched or unbranched $C_2$–$C_6$ alkenyl or alkynyl, $C_3$–$C_7$ cycloalkyl, aryl, aryl-($C_1$–$C_6$)-alkyl, $CO_2R_{14}$, $CON(R_{14})_2$, substituted $C_1$–$C_6$ alkyl, substituted aryl, wherein the substituent is $N(R_{14})_2$, halogen, $OR_{14}$ or $SR_{14}$;

wherein $R_8$ is H or $CH_3$;

wherein $R_{10}$ is H or F;

wherein $R_{11}$ is H, F, Cl, Br, I, CN, branched or unbranched $C_1$–$C_6$ alkyl or alkoxy;

wherein $R_{13}$ is H or F;

and wherein $R_{14}$ is independently H or branched or unbranched $C_1$–$C_6$ alkyl.

2. The method of claim 1, wherein the compound has the structure:

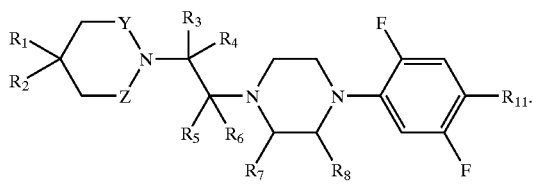

3. The method of claim 2, wherein the compound has the structure:

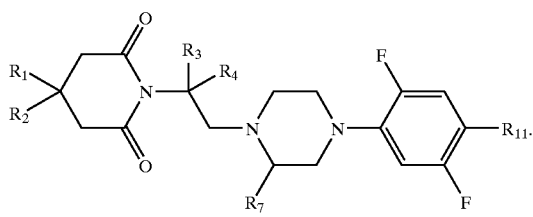

4. The method of claim 3, wherein the compound has the structure:

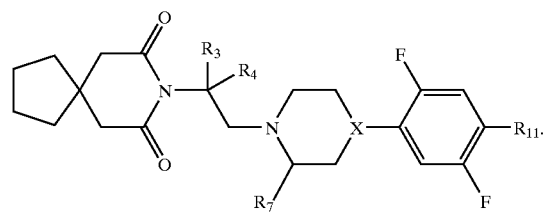

5. The method of claim 4, wherein the compound has the structure:

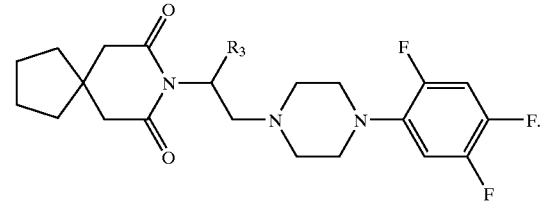

6. The method of claim 5, wherein the compound has the structure:

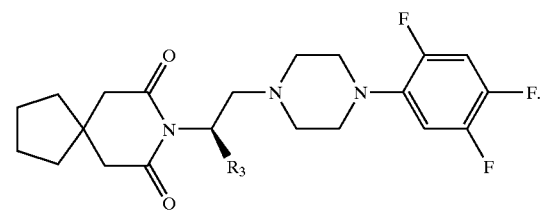

7. A compound having the structure:

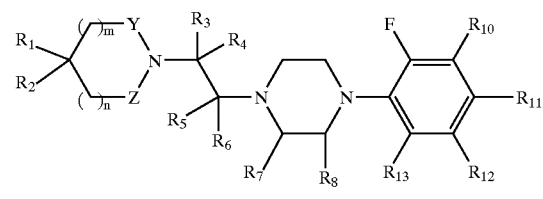

wherein each m and n is independently an integer from 0 to 2;

wherein each Y and Z is independently

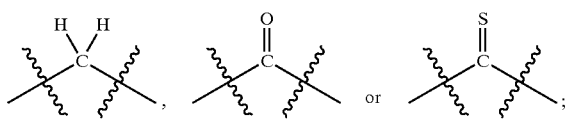

wherein $R_1$ and $R_2$ (i) are independently H, branched or unbranched $C_1$–$C_6$ alkyl or alkoxy, branched or unbranched $C_2$–$C_6$ alkenyl or alkynyl, branched or unbranched $C_1$–$C_6$ hydroxyalkyl, hydroxy, substituted or unsubstituted aryl or aryl-($C_1$–$C_6$)-alkyl, or substituted or unsubstituted heteroaryl or heteroaryl-($C_1$–$C_6$)-alkyl, wherein the substituent if present is a halogen, CN, nitro, hydroxy, branched or unbranched $C_1$–$C_6$ alkyl or alkoxy group, or branched or unbranched $C_2$–$C_6$ alkenyl or alkynyl group; or (ii) taken together form a substituted or unsubstituted cycloalkyl ring containing 3–10 carbons, wherein the substituent if present is a branched or unbranched $C_1$–$C_6$ alkyl group or branched or unbranched $C_2$–$C_6$ alkenyl or alkynyl group;

wherein $R_3$ is H, branched or unbranched $C_1$–$C_6$ alkyl, branched or unbranched $C_2$–$C_6$ alkenyl or alkynyl, $C_3$–$C_7$ cycloalkyl, $C_3$–$C_7$ cycloalkylalkyl, aryl, heteroaryl, aryl-($C_1$–$C_6$)-alkyl, heteroaryl-($C_1$–$C_6$)-alkyl, substituted $C_3$–$C_7$ cycloalkyl, substituted aryl, substituted heteroaryl, substituted aryl-($C_1$–$C_6$)-alkyl, or substituted heteroaryl-($C_1$–$C_6$)-alkyl, wherein the substituent if present is a halogen, CN, nitro, $C_1$–$C_6$ alkyl, $OR_{14}$, $SR_{14}$, $N(R_{14})_2$, $SO_2N(R_{14})_2$, $CO_2R_{14}$, $SO_3R_{14}$, $N(R_{14})COR_{14}$, $CON(R_{14})_2$, or $N(R_{14})CON(R_{14})_2$;

wherein $R_4$ is H or $CH_3$;

wherein $R_5$ is H, branched or unbranched $C_1$–$C_6$ alkyl, branched or unbranched $C_2$–$C_6$ alkenyl or alkynyl, $C_3$–$C_7$ cycloalkyl, $C_3$–$C_7$ cycloalkylalkyl, aryl, heteroaryl, aryl-($C_1$–$C_6$)-alkyl, heteroaryl-($C_1$–$C_6$)-alkyl, substituted $C_1$–$C_6$ alkyl, substituted $C_3$–$C_7$ cycloalkyl, substituted aryl, substituted heteroaryl, substituted aryl-($C_1$–$C_6$)-alkyl, or substituted heteroaryl-($C_1$–$C_6$)-alkyl, wherein the substituent if present is a halogen, CN, nitro, $C_1$–$C_6$ alkyl, $OR_{14}$, $SR_{14}$, $N(R_{14})_2$, $SO_2N(R_{14})_2$, $CO_2R_{14}$, $SO_3R_{14}$, $N(R_{14})COR_{14}$, $CON(R_{14})_2$, or $N(R_{14})CON(R_{14})_2$;

wherein $R_6$ is H, branched or unbranched $C_1$–$C_6$ alkyl, branched or unbranched $C_2$–$C_6$ alkenyl or alkynyl, $C_3$–$C_7$ cycloalkyl, $C_3$–$C_7$ cycloalkylalkyl, aryl, heteroaryl, aryl-($C_1$–$C_6$)-alkyl, heteroaryl-($C_1$–$C_6$)-alkyl, substituted $C_1$–$C_6$ alkyl, substituted $C_3$–$C_7$ cycloalkyl, substituted aryl, substituted heteroaryl, substituted aryl-($C_1$–$C_6$)-alkyl, or substituted heteroaryl-($C_1$–$C_6$)-alkyl, wherein the substituent if present is a halogen, CN, nitro, $C_1$–$C_6$ alkyl, $OR_{14}$, $SR_{14}$, $N(R_{14})_2$, $SO_2N(R_{14})_2$, $CO_2R_{14}$, $SO_3R_{14}$, $N(R_{14})COR_{14}$, $CON(R_{14})_2$, or $N(R_{14})CON(R_{14})_2$;

wherein $R_7$ is H, branched or unbranched $C_1$–$C_6$ alkyl, branched or unbranched $C_2$–$C_6$ alkenyl or alkynyl, $C_3$–$C_7$ cycloalkyl, aryl, aryl-($C_1$–$C_6$)-alkyl, $CO_2R_{14}$, $CON(R_{14})_2$, substituted $C_1$–$C_6$ alkyl, substituted aryl, wherein the substituent is $N(R_{14})2$, halogen, $OR_{14}$ or $SR_{14}$;

wherein $R_8$ is H or $CH_3$;

wherein $R_{10}$ is H or F;

wherein $R_{11}$ is H, F, Cl, Br, I, CN, branched or unbranched $C_1$–$C_6$ alkyl or alkoxy;

wherein $R_{13}$ is H or F;

and wherein $R_{14}$ is independently H or branched or unbranched $C_1$–$C_6$ alkyl.

8. A compound of claim 7, wherein the compound has the structure:

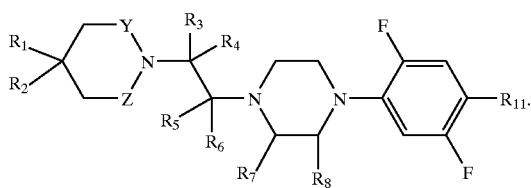

9. A compound of claim 8, wherein the compound has the structure:

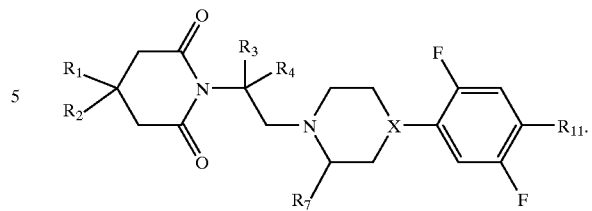

10. A compound of claim 9, wherein the compound has the structure:

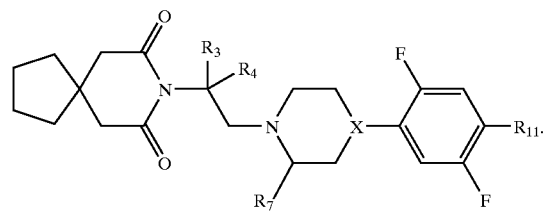

11. A compound of claim 10, wherein the compound has the structure:

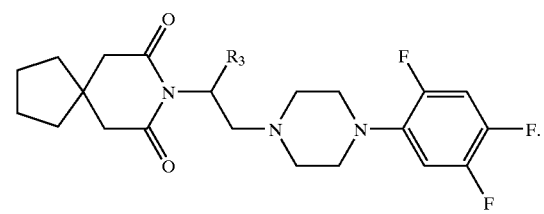

12. A compound of claim 11, wherein the compound has the structure:

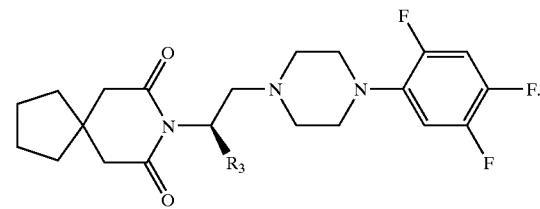

13. A pharmaceutical composition comprising a therapeutically effective amount of the compound of claim 7 and a pharmaceutically acceptable carrier.

14. The pharmaceutical composition of claim 13, wherein the amount of the compound is an amount from about 0.01 mg to about 800 mg.

15. The pharmaceutical composition of claim 14, wherein the amount of the compound is from about 0.1 mg to about 300 mg.

16. The pharmaceutical composition of claim 15, wherein the amount of the compound is from about 1 mg to about 20 mg.

17. The pharmaceutical composition of claim 13, wherein the carrier is a liquid.

18. The pharmaceutical composition of claim 13, wherein the carrier is a solid.

19. The pharmaceutical composition of claim 13, wherein the carrier is a gel.

20. A pharmaceutical composition obtained by combining a therapeutically effective amount of a compound of claim 7 and a pharmaceutically acceptable carrier.

21. A process for making a pharmaceutical composition comprising combining a therapeutically effective amount of a compound of claim 7 and a pharmaceutically acceptable carrier.

22. A process of making a compound with structure:

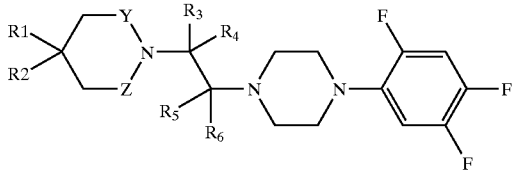

which comprises reacting a compound with structure:

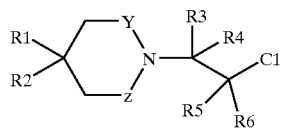

with a compound

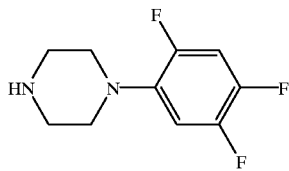

to form the compound,
wherein Y is

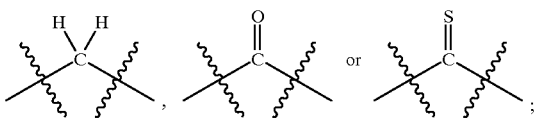

wherein Z is

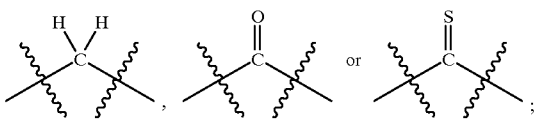

wherein R1 and R2 (i) are independently H, branched or unbranched $C_1$–$C_6$ alkyl or alkoxy, branched or unbranched $C_2$–$C_6$ alkenyl or alkynyl, branched or unbranched $C_1$–$C_6$, hydroxyalkyl, hydroxy, substituted or unsubstituted aryl or aryl-($C_1$–$C_6$)-alkyl, or substituted or unsubstituted heteroaryl or heteroaryl-($C_1$–$C_6$)-alkyl, wherein the substituent if present is a halogen, CN, nitro, hydroxy, branched or unbranched $C_1$–$C_6$ alkyl or alkoxy group, or branched or unbranched $C_2$–$C_6$ alkenyl or alkynyl group; or (ii) taken together form a substituted or unsubstituted cycloalkyl ring containing 3–10 carbons, wherein the substituent if present is a branched or unbranched $C_1$–$C_6$ alkyl group or branched or unbranched $C_2$–$C_6$ alkenyl or alkynyl group;

wherein R3 is H, branched or unbranched $C_1$–$C_6$ alkyl, branched or unbranched $C_2$–$C_6$ alkenyl or alkynyl, $C_3$–$C_7$ cycloalkyl, $C_3$–$C_7$ cycloalkylalkyl, aryl, heteroaryl, aryl-($C_1$–$C_6$)-alkyl, heteroaryl-($C_1$–$C_6$)-alkyl, substituted $C_1$–$C_6$ alkyl, substituted $C_3$–$C_7$ cycloalkyl, substituted aryl, substituted heteroaryl, substituted aryl-($C_1$–$C_6$)-alkyl, or substituted heteroaryl-($C_1$–$C_6$)-alkyl, wherein the substituent if present is a halogen, CN, nitro, $C_1$–$C_6$ alkyl, OR14, SR14, N(R14)$_2$, SO$_2$N(R14)$_2$, CO$_2$R14, SO$_3$R14, N(R14)COR14, CON(R14)$_2$, or N(R14)CON(R14)$_2$;

wherein R4 is H or $CH_3$;

wherein R5 is H, branched or unbranched $C_1$–$C_6$ alkyl, branched or unbranched $C_2$–$C_6$ alkenyl or alkynyl, $C_3$–$C_7$ cycloalkyl, $C_3$–$C_7$ cycloalkylalkyl, aryl, heteroaryl, aryl-($C_1$–$C_6$)-alkyl, heteroaryl-($C_1$–$C_6$)-alkyl, substituted $C_1$–$C_6$ alkyl, substituted $C_3$–$C_7$ cycloalkyl, substituted aryl, substituted heteroaryl, substituted aryl-($C_1$–$C_6$)-alkyl, or substituted heteroaryl-($C_1$–$C_6$)-alkyl, wherein the substituent if present is a halogen, CN, nitro, $C_1$–$C_6$ alkyl, OR14, SR14, N(R14)$_2$, SO$_2$N(R14)$_2$, CO$_2$R14, SO$_3$R14, N(R14)COR14, CON(R14)$_2$, or N(R14)CON(R14)$_2$;

wherein R6 is H, branched or unbranched $C_1$–$C_6$ alkyl, branched or unbranched $C_2$–$C_6$ alkenyl or alkynyl, $C_3$–$C_7$ cycloalkyl, $C_3$–$C_7$ cycloalkylalkyl, aryl, heteroaryl, aryl-($C_1$–$C_6$)-alkyl, heteroaryl-($C_1$–$C_6$)-alkyl, substituted $C_1$–$C_6$ alkyl, substituted $C_3$–$C_7$ cycloalkyl, substituted aryl, substituted heteroaryl, substituted aryl-($C_1$–$C_6$)-alkyl, or substituted heteroaryl-($C_1$–$C_6$)-alkyl, wherein the substituent if present is a halogen, CN, nitro, $C_1$–$C_6$ alkyl, OR14, SR14, N(R14)$_2$, SO$_2$N(R14)$_2$, CO$_2$R14, SO$_3$R14, N(R14)COR14, CON(R14)$_2$, or N(R14)CON(R14)$_2$; and wherein R14 is independently H or branched or unbranched $C_1$–$C_6$ alkyl.

23. A method of treating a subject afflicted with a disease which is susceptible to treatment by antagonism of the human $\alpha_{1d}$ adrenergic receptor which comprises administering to the subject an amount of the compound of claim 7 effective to treat the disease.

24. A method of treating a subject afflicted with hypertension which comprises administering to the subject an amount of the compound of claim 7 effective to treat the disease.

25. A method of treating a subject afflicted with Raynaud's disease which comprises administering to the subject an amount of the compound of claim 7 effective to treat the disease.

26. A method of claim 25, wherein the compound additionally does not cause hypotension at dosages effective to treat Raynaud's disease.

27. A method of treating a subject afflicted with urinary incontinence which comprises administering to the subject an amount of the compound of claim 7 effective to treat the disease.

28. A method of claim 27, wherein the compound additionally does not cause hypotension at dosages effective to treat urinary incontinence.

29. A method of treating urinary incontinence in a subject which comprises administering to the subject a therapeutically effective amount of a $\alpha_{1d}$ adrenergic receptor antagonist, which binds to the human $\alpha_{1d}$ adrenergic receptor with a binding affinity which is at least 10-fold higher than the binding affinity with which the compound binds to (i) a human $\alpha_{1a}$ adrenergic receptor and (ii) a human $\alpha_{1b}$ adrenergic receptor, and the $\alpha_{1d}$ antagonist binds to the human $\alpha_{1d}$ adrenergic receptor with a binding affinity which is at least ten-fold higher than the binding affinity with which the compound binds to a human 5-HT$_{1a}$ receptor, wherein the $\alpha_{1d}$ adrenergic receptor antagonist has the structure:

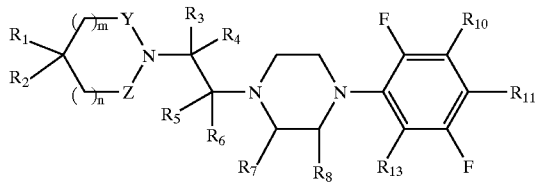

wherein each m and n is independently an integer from 0 to 2;

wherein each Y and Z is independently

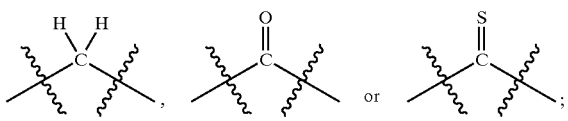

wherein R1 and R2 (i) are independently H, branched or unbranched $C_1$–$C_6$ alkyl or alkoxy, branched or unbranched $C_2$–$C_6$ alkenyl or alkynyl, branched or unbranched $C_1$–$C_6$ hydroxyalkyl, hydroxy, substituted or unsubstituted aryl or aryl-($C_1$–$C_6$)-alkyl, or unsubstituted heteroaryl or heteroaryl-($C_1$–$C_6$)-alkyl, wherein the substituent if present is a halogen, CN, nitro, hydroxy, branched or unbranched $C_1$–$C_6$ alkyl or alkoxy group, or branched or unbranched $C_2$–$C_6$ alkenyl or alkynyl group; or (ii) taken together form a substituted or unsubstituted cycloalkyl ring containing 3–10 carbons, wherein the substituent if present is a branched or unbranched $C_1$–$C_6$ alkyl group or branched or unbranched $C_2$–$C_6$ alkenyl or alkynyl group;

wherein R3 is H, branched or unbranched $C_1$–$C_6$ alkyl, branched or unbranched $C_2$–$C_6$ alkenyl or alkynyl, $C_3$–$C_7$ cycloalkyl, $C_3$–$C_7$ cycloalkylalkyl, aryl, heteroaryl, aryl-($C_1$–$C_6$)-alkyl, heteroaryl-($C_1$–$C_6$)-alkyl, substituted $C_1$–$C_6$ alkyl, substituted $C_3$–$C_7$ cycloalkyl, substituted aryl, substituted heteroaryl, substituted aryl-($C_1$–$C_6$)-alkyl, or substituted heteroaryl-($C_1$–$C_6$)-alkyl, wherein the substituent if present is a halogen, CN, nitro, $C_1$–$C_6$ alkyl, OR14, SR14, N(R14)$_2$, SO$_2$N(R14)$_2$, CO$_2$R14, SO$_3$R14, N(R14)COR14, CON(R14)$_2$, or N(R14)CON(R14)$_2$;

wherein R4 is H or CH$_3$;

wherein R5 is H, branched or unbranched $C_1$–$C_6$ alkyl, branched or unbranched $C_2$–$C_6$ alkenyl or alkynyl, $C_3$–$C_7$ cycloalkyl, $C_3$–$C_7$ cycloalkylalkyl, aryl, heteroaryl, aryl-($C_1$–$C_6$)-alkyl, heteroaryl-($C_1$–$C_6$)-alkyl, substituted $C_1$–$C_6$ alkyl, substituted $C_3$–$C_7$ cycloalkyl, substituted aryl, substituted heteroaryl, substituted aryl-($C_1$–$C_6$)-alkyl, or substituted heteroaryl-($C_1$–$C_6$)-alkyl, wherein the substituent if present is a halogen, CN, nitro, $C_1$–$C_6$ alkyl, OR14, SR14, N(R14)$_2$, SO$_2$N(R14)$_2$, CO$_2$R14, SO$_3$R14, N(R14)COR14, CON(R14)$_2$, or N(R14)CON(R14)$_2$;

wherein R6 is H, branched or unbranched $C_1$–$C_6$ alkyl, branched or unbranched $C_2$–$C_6$ alkenyl or alkynyl, $C_3$–$C_7$ cycloalkyl, $C_3$–$C_7$ cycloalkylalkyl, aryl, heteroaryl, aryl-($C_1$–$C_6$)-alkyl, heteroaryl-($C_1$–$C_6$)-alkyl, substituted $C_1$–$C_6$ alkyl, substituted $C_3$–$C_7$ cycloalkyl, substituted aryl, substituted heteroaryl, substituted aryl-($C_1$–$C_6$)-alkyl, or substituted heteroaryl-($C_1$–$C_6$)-alkyl, wherein the substituent if present is a halogen, CN, nitro, $C_1$–$C_6$ alkyl, OR14, SR14, N(R14)$_2$, SO$_2$N(R14)$_2$, CO$_2$R14, SO$_3$R14, N(R14)COR14, CON(R14)$_2$, or N(R14)CON(R14)$_2$;

wherein R7 is H, branched or unbranched $C_1$–$C_6$ alkyl, branched or unbranched $C_2$–$C_6$ alkenyl or alkynyl, $C_3$–$C_7$ cycloalkyl, aryl, aryl-($C_1$–$C_6$)-alkyl, CO$_2$R14, CON(R14)$_2$, substituted $C_1$–$C_6$ alkyl, substituted aryl, wherein the substituent is N(R14)$_2$, halogen, OR14 or SR14;

wherein R8 is H or CH$_3$;

wherein R10 is H or F; wherein R11 is H, F, Cl, Br, I, CN, branched or unbranched $C_1$–$C_6$ alkyl or alkoxy; wherein R13 is H or F;

and wherein R14 is independently H or branched or unbranched $C_1$–$C_6$ alkyl.

30. The method of claim 29, wherein the $\alpha_{1d}$ antagonist binds to the human $\alpha_{1d}$ adrenergic receptor with a binding affinity which is at least 25-fold higher than the binding affinity with which the $\alpha_{1d}$ antagonist binds to (i) the human $\alpha_{1a}$ adrenergic receptor and (ii) the human $\alpha_{1b}$ adrenergic receptor, and the $\alpha_{1d}$ antagonist binds to the human $\alpha_{1d}$ adrenergic receptor with a binding affinity which is at least ten-fold higher than the binding affinity with which the $\alpha_{1d}$ antagonist binds to the human 5-HT$_{1a}$ receptor.

31. The method of claim 30, wherein the $\alpha_{1d}$ antagonist binds to the human $\alpha_{1d}$ adrenergic receptor with a binding affinity which is at least 25-fold higher than the binding affinity with which the $\alpha_{1d}$ antagonist binds to (i) the human $\alpha_{1a}$ adrenergic receptor, (ii) the human $\alpha_{1b}$ adrenergic receptor, and (iii) the human 5-HT$_{1a}$ receptor.

32. The method of claim 31, wherein the $\alpha_{1d}$ antagonist binds to the human $\alpha_{1d}$ adrenergic receptor with a binding affinity which is at least 100-fold higher than the binding affinity with which the $\alpha_{1d}$ antagonist binds to (i) the human $\alpha_{1a}$ adrenergic receptor, (ii) the human $\alpha_{1b}$ adrenergic receptor, and (iii) the human 5-HT$_{1a}$ receptor.

33. A method of claim 38, wherein the $\alpha_{1d}$ antagonist additionally does not cause hypotension at dosages effective to treat urinary incontinence.

34. The compound of claim 7, wherein the compound comprises the (−) enantiomer.

35. The compound of claim 7, wherein the compound comprises the (+) enantiomer.

36. The method of claim 1, wherein the compound binds to the human $\alpha_{1d}$ adrenergic receptor with a binding affinity which is at least 25-fold higher than the binding affinity with which the compound binds to (i) the human $\alpha_{1a}$ adrenergic receptor and (ii) the human $\alpha_{1b}$ adrenergic receptor, and the compound binds to the human $\alpha_{1d}$ adrenergic receptor with a binding affinity which is at least ten-fold higher than the binding affinity with which the compound binds to the human 5-HT$_{1a}$ receptor.

37. The method of claim 36, wherein the compound binds to the human $\alpha_{1d}$ adrenergic receptor with a binding affinity which is at least 25-fold higher than the binding affinity with which the compound binds to (i) the human $\alpha_{1a}$ adrenergic receptor, (ii) the human $\alpha_{1b}$ adrenergic receptor, and (iii) the human 5-HT$_{1a}$ receptor.

38. The method of claim 37, wherein the compound binds to the human $\alpha_{1d}$ adrenergic receptor with a binding affinity which is at least 100-fold higher than the binding affinity with which the compound binds to (i) the human $\alpha_{1a}$ adrenergic receptor, (ii) the human $\alpha_{1b}$ adrenergic receptor, and (iii) the human 5-HT$_{1a}$ receptor.

* * * * *